(12) United States Patent
Witt et al.

(10) Patent No.: US 10,265,094 B2
(45) Date of Patent: *Apr. 23, 2019

(54) ULTRASONIC SURGICAL BLADES

(71) Applicant: Ethicon LLC, Guaynabo, PR (US)

(72) Inventors: David A. Witt, Maineville, OH (US); Jeffrey D. Messerly, Cincinnati, OH (US); Kevin L. Houser, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/006,373

(22) Filed: Jun. 12, 2018

(65) Prior Publication Data

US 2018/0289389 A1 Oct. 11, 2018

Related U.S. Application Data

(63) Continuation of application No. 15/477,861, filed on Apr. 3, 2017, now Pat. No. 10,045,794, which is a
(Continued)

(51) Int. Cl.
*A61B 17/32* (2006.01)
*A61N 7/00* (2006.01)
*A61L 31/08* (2006.01)
*A61L 31/10* (2006.01)
*A61L 31/14* (2006.01)
(Continued)

(52) U.S. Cl.
CPC .... *A61B 17/320092* (2013.01); *A61L 31/088* (2013.01); *A61L 31/10* (2013.01); *A61L 31/14* (2013.01); *A61N 7/00* (2013.01); *A61B 17/320068* (2013.01); *A61B 2017/0088* (2013.01); *A61B 2017/00849* (2013.01); *A61B 2017/00853* (2013.01);
(Continued)

(58) Field of Classification Search
CPC ............................................ A61B 2017/32116
USPC .................................. 606/45; 427/299, 2.25
See application file for complete search history.

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| AU | 2003241752 A1 | 9/2003 |
| CA | 2535467 A1 | 4/1993 |

(Continued)

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
(Continued)

*Primary Examiner* — Cachet I Sellman

(57) ABSTRACT

An ultrasonic surgical blade includes a body having a proximal end, a distal end, and an outer surface. The distal end is movable relative to a longitudinal axis in accordance with ultrasonic vibrations applied to the proximal end. At least a portion of the outer surface of the body comprises a lubricious coating adhered thereto. The lubricious coating has a coefficient of friction that is less than the coefficient of friction of the outer surface of the body.

18 Claims, 10 Drawing Sheets

Related U.S. Application Data continuation of application No. 12/274,884, filed on Nov. 20, 2008, now Pat. No. 10,010,339.

(60) Provisional application No. 61/004,961, filed on Nov. 30, 2007.

(51) Int. Cl.
    *A61B 17/00* (2006.01)
    *A61N 7/02* (2006.01)

(52) U.S. Cl.
    CPC ............ *A61B 2017/320078* (2017.08); *A61L 2400/10* (2013.01); *A61N 7/02* (2013.01)

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |

(56) References Cited

U.S. PATENT DOCUMENTS

| | | | |
|---|---|---|---|
| 4,983,160 A * | 1/1991 | Steppe | A61F 9/00745 604/22 |
| 5,013,956 A | 5/1991 | Kurozumi et al. | |
| 5,015,227 A | 5/1991 | Broadwin et al. | |
| 5,020,514 A | 6/1991 | Heckele | |
| 5,026,370 A | 6/1991 | Lottick | |
| 5,026,387 A | 6/1991 | Thomas | |
| 5,035,695 A | 7/1991 | Weber, Jr. et al. | |
| 5,042,707 A | 8/1991 | Taheri | |
| 5,061,269 A | 10/1991 | Muller | |
| 5,084,052 A | 1/1992 | Jacobs | |
| 5,099,840 A | 3/1992 | Goble et al. | |
| 5,104,025 A | 4/1992 | Main et al. | |
| 5,105,117 A | 4/1992 | Yamaguchi | |
| 5,106,538 A | 4/1992 | Barma et al. | |
| 5,108,383 A | 4/1992 | White | |
| 5,109,819 A | 5/1992 | Custer et al. | |
| 5,112,300 A | 5/1992 | Ureche | |
| 5,123,903 A | 6/1992 | Quaid et al. | |
| 5,126,618 A | 6/1992 | Takahashi et al. | |
| D327,872 S | 7/1992 | McMills et al. | |
| 5,152,762 A | 10/1992 | McElhenney | |
| 5,156,633 A | 10/1992 | Smith | |
| 5,160,334 A | 11/1992 | Billings et al. | |
| 5,162,044 A | 11/1992 | Gahn et al. | |
| 5,163,421 A | 11/1992 | Bernstein et al. | |
| 5,163,537 A | 11/1992 | Radev | |
| 5,167,619 A | 12/1992 | Wuchinich | |
| 5,167,725 A | 12/1992 | Clark et al. | |
| 5,172,344 A | 12/1992 | Ehrlich | |
| 5,174,276 A | 12/1992 | Crockard | |
| D332,660 S | 1/1993 | Rawson et al. | |
| 5,176,677 A | 1/1993 | Wuchinich | |
| 5,176,695 A | 1/1993 | Dulebohn | |
| 5,184,605 A | 2/1993 | Grzeszykowski | |
| 5,188,102 A | 2/1993 | Idemoto et al. | |
| D334,173 S | 3/1993 | Liu et al. | |
| 5,190,541 A | 3/1993 | Abele et al. | |
| 5,196,007 A | 3/1993 | Ellman et al. | |
| 5,205,459 A | 4/1993 | Brinkerhoff et al. | |
| 5,209,719 A | 5/1993 | Baruch et al. | |
| 5,213,569 A | 5/1993 | Davis | |
| 5,214,339 A | 5/1993 | Naito | |
| 5,217,460 A | 6/1993 | Knoepfler | |
| 5,218,529 A | 6/1993 | Meyer et al. | |
| 5,221,282 A | 6/1993 | Wuchinich | |
| 5,222,937 A | 6/1993 | Kagawa | |
| 5,226,909 A | 7/1993 | Evans et al. | |
| 5,226,910 A | 7/1993 | Kajiyama et al. | |
| 5,234,428 A | 8/1993 | Kaufman | |
| 5,234,436 A | 8/1993 | Eaton et al. | |
| 5,241,236 A | 8/1993 | Sasaki et al. | |
| 5,241,968 A | 9/1993 | Slater | |
| 5,242,460 A | 9/1993 | Klein et al. | |
| 5,254,129 A | 10/1993 | Alexander | |
| 5,257,988 A | 11/1993 | L'Esperance, Jr. | |
| 5,258,006 A | 11/1993 | Rydell et al. | |
| 5,261,922 A | 11/1993 | Hood | |
| 5,263,957 A | 11/1993 | Davison | |
| 5,264,925 A | 11/1993 | Shipp et al. | |
| 5,275,166 A | 1/1994 | Vaitekunas et al. | |
| 5,275,607 A | 1/1994 | Lo et al. | |
| 5,275,609 A | 1/1994 | Pingleton et al. | |
| 5,282,800 A | 2/1994 | Foshee et al. | |
| 5,282,817 A | 2/1994 | Hoogeboom et al. | |
| 5,285,795 A | 2/1994 | Ryan et al. | |
| 5,285,945 A | 2/1994 | Brinkerhoff et al. | |
| 5,290,286 A | 3/1994 | Parins | |
| 5,300,068 A | 4/1994 | Rosar et al. | |
| 5,304,115 A | 4/1994 | Pflueger et al. | |
| D347,474 S | 5/1994 | Olson | |
| 5,307,976 A | 5/1994 | Olson et al. | |
| 5,309,927 A | 5/1994 | Welch | |
| 5,312,023 A | 5/1994 | Green et al. | |
| 5,312,425 A | 5/1994 | Evans et al. | |
| 5,318,563 A | 6/1994 | Malis et al. | |
| 5,318,564 A | 6/1994 | Eggers | |
| 5,318,570 A | 6/1994 | Hood et al. | |
| 5,318,589 A | 6/1994 | Lichtman | |
| 5,322,055 A | 6/1994 | Davison et al. | |
| 5,324,299 A | 6/1994 | Davison et al. | |
| 5,326,013 A | 7/1994 | Green et al. | |
| 5,326,342 A | 7/1994 | Pflueger et al. | |
| 5,330,471 A | 7/1994 | Eggers | |
| 5,330,502 A | 7/1994 | Hassler et al. | |
| 5,339,723 A | 8/1994 | Huitema | |
| 5,342,359 A | 8/1994 | Rydell | |
| 5,344,420 A | 9/1994 | Hilal et al. | |
| 5,345,937 A | 9/1994 | Middleman et al. | |
| 5,346,502 A | 9/1994 | Estabrook et al. | |
| 5,353,474 A | 10/1994 | Good et al. | |
| 5,357,164 A | 10/1994 | Imabayashi et al. | |
| 5,357,423 A | 10/1994 | Weaver et al. | |
| 5,359,994 A | 11/1994 | Krauter et al. | |
| 5,361,583 A | 11/1994 | Huitema | |
| 5,366,466 A | 11/1994 | Christian et al. | |
| 5,368,557 A | 11/1994 | Nita et al. | |
| 5,370,645 A | 12/1994 | Klicek et al. | |
| 5,371,429 A | 12/1994 | Manna | |
| 5,374,813 A | 12/1994 | Shipp | |
| D354,564 S | 1/1995 | Medema | |
| 5,381,067 A | 1/1995 | Greenstein et al. | |
| 5,383,874 A | 1/1995 | Jackson et al. | |
| 5,387,207 A | 2/1995 | Dyer et al. | |
| 5,387,215 A | 2/1995 | Fisher | |
| 5,389,098 A | 2/1995 | Tsuruta et al. | |
| 5,394,187 A | 2/1995 | Shipp | |
| 5,395,312 A | 3/1995 | Desai | |
| 5,395,363 A | 3/1995 | Billings et al. | |
| 5,395,364 A | 3/1995 | Anderhub et al. | |
| 5,396,266 A | 3/1995 | Brimhall | |
| 5,396,900 A | 3/1995 | Slater et al. | |
| 5,403,312 A | 4/1995 | Yates et al. | |
| 5,403,334 A | 4/1995 | Evans et al. | |
| 5,408,268 A | 4/1995 | Shipp | |
| D358,887 S | 5/1995 | Feinberg | |
| 5,411,481 A | 5/1995 | Allen et al. | |
| 5,417,709 A | 5/1995 | Slater | |
| 5,419,761 A | 5/1995 | Narayanan et al. | |
| 5,421,829 A | 6/1995 | Olichney et al. | |
| 5,423,844 A | 6/1995 | Miller | |
| 5,428,504 A | 6/1995 | Bhatla | |
| 5,429,131 A | 7/1995 | Scheinman et al. | |
| 5,438,997 A | 8/1995 | Sieben et al. | |
| 5,443,463 A | 8/1995 | Stern et al. | |
| 5,445,638 A | 8/1995 | Rydell et al. | |
| 5,445,639 A | 8/1995 | Kuslich et al. | |
| 5,449,370 A | 9/1995 | Vaitekunas | |
| 5,451,220 A | 9/1995 | Ciervo | |
| 5,451,227 A | 9/1995 | Michaelson | |
| 5,456,684 A | 10/1995 | Schmidt et al. | |
| 5,458,598 A | 10/1995 | Feinberg et al. | |
| 5,465,895 A | 11/1995 | Knodel et al. | |
| 5,471,988 A | 12/1995 | Fujio et al. | |
| 5,472,443 A | 12/1995 | Cordis et al. | |
| 5,476,479 A | 12/1995 | Green et al. | |
| 5,478,003 A | 12/1995 | Green et al. | |
| 5,480,409 A | 1/1996 | Riza | |
| 5,483,501 A | 1/1996 | Park et al. | |
| 5,484,436 A | 1/1996 | Eggers et al. | |
| 5,486,162 A | 1/1996 | Brumbach | |
| 5,486,189 A | 1/1996 | Mudry et al. | |
| 5,490,860 A | 2/1996 | Middle et al. | |
| 5,496,317 A | 3/1996 | Goble et al. | |
| 5,500,216 A | 3/1996 | Julian et al. | |
| 5,501,654 A | 3/1996 | Failla et al. | |
| 5,504,650 A | 4/1996 | Katsui et al. | |
| 5,505,693 A * | 4/1996 | Mackool | A61F 9/00745 604/22 |
| 5,507,738 A | 4/1996 | Ciervo | |
| 5,509,922 A | 4/1996 | Aranyi et al. | |
| 5,511,556 A | 4/1996 | DeSantis | |
| 5,520,704 A | 5/1996 | Castro et al. | |
| 5,522,839 A | 6/1996 | Pilling | |

(56) References Cited

U.S. PATENT DOCUMENTS

| | | |
|---|---|---|
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,155 A | 7/1998 | Beaupre et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,959 A | 8/1998 | Castro et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |

(56) References Cited

U.S. PATENT DOCUMENTS

| | | | |
|---|---|---|---|
| 5,993,465 A | 11/1999 | Shipp et al. | |
| 5,993,972 A | 11/1999 | Reich et al. | |
| 5,994,855 A | 11/1999 | Lundell et al. | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,024,750 A * | 2/2000 | Mastri | A61B 17/29 606/169 |
| 6,027,515 A | 2/2000 | Cimino | |
| 6,031,526 A | 2/2000 | Shipp | |
| 6,033,375 A | 3/2000 | Brumbach | |
| 6,033,399 A | 3/2000 | Gines | |
| 6,036,667 A | 3/2000 | Manna et al. | |
| 6,036,707 A | 3/2000 | Spaulding | |
| 6,039,734 A | 3/2000 | Goble | |
| 6,048,224 A | 4/2000 | Kay | |
| 6,050,943 A | 4/2000 | Slayton et al. | |
| 6,050,996 A | 4/2000 | Schmaltz et al. | |
| 6,051,010 A | 4/2000 | DiMatteo et al. | |
| 6,056,735 A | 5/2000 | Okada et al. | |
| 6,063,098 A | 5/2000 | Houser et al. | |
| 6,066,132 A | 5/2000 | Chen et al. | |
| 6,066,151 A | 5/2000 | Miyawaki et al. | |
| 6,068,627 A | 5/2000 | Orszulak et al. | |
| 6,068,629 A | 5/2000 | Haissaguerre et al. | |
| 6,068,647 A | 5/2000 | Witt et al. | |
| 6,074,389 A | 6/2000 | Levine et al. | |
| 6,077,285 A | 6/2000 | Boukhny | |
| 6,083,191 A | 7/2000 | Rose | |
| 6,086,584 A | 7/2000 | Miller | |
| 6,090,120 A | 7/2000 | Wright et al. | |
| 6,091,995 A | 7/2000 | Ingle et al. | |
| 6,096,033 A | 8/2000 | Tu et al. | |
| 6,099,483 A | 8/2000 | Palmer et al. | |
| 6,099,542 A | 8/2000 | Cohn et al. | |
| 6,099,550 A | 8/2000 | Yoon | |
| 6,109,500 A | 8/2000 | Alli et al. | |
| 6,110,127 A | 8/2000 | Suzuki | |
| 6,113,594 A | 9/2000 | Savage | |
| 6,117,152 A | 9/2000 | Huitema | |
| H1904 H | 10/2000 | Yates et al. | |
| 6,126,629 A | 10/2000 | Perkins | |
| 6,129,735 A | 10/2000 | Okada et al. | |
| 6,129,740 A | 10/2000 | Michelson | |
| 6,132,368 A | 10/2000 | Cooper | |
| 6,132,427 A | 10/2000 | Jones et al. | |
| 6,132,448 A | 10/2000 | Perez et al. | |
| 6,139,320 A | 10/2000 | Hahn | |
| 6,139,561 A | 10/2000 | Shibata et al. | |
| 6,142,615 A | 11/2000 | Qiu et al. | |
| 6,142,994 A | 11/2000 | Swanson et al. | |
| 6,144,402 A | 11/2000 | Norsworthy et al. | |
| 6,147,560 A | 11/2000 | Erhage et al. | |
| 6,152,902 A | 11/2000 | Christian et al. | |
| 6,152,923 A | 11/2000 | Ryan | |
| 6,154,198 A | 11/2000 | Rosenberg | |
| 6,156,029 A | 12/2000 | Mueller | |
| 6,159,160 A | 12/2000 | Hsei et al. | |
| 6,159,175 A | 12/2000 | Strukel et al. | |
| 6,162,194 A | 12/2000 | Shipp | |
| 6,162,208 A | 12/2000 | Hipps | |
| 6,165,150 A | 12/2000 | Banko | |
| 6,174,309 B1 | 1/2001 | Wrublewski et al. | |
| 6,174,310 B1 | 1/2001 | Kirwan, Jr. | |
| 6,176,857 B1 | 1/2001 | Ashley | |
| 6,179,853 B1 | 1/2001 | Sachse et al. | |
| 6,183,426 B1 | 2/2001 | Akisada et al. | |
| 6,190,386 B1 | 2/2001 | Rydell | |
| 6,193,709 B1 | 2/2001 | Miyawaki et al. | |
| 6,204,592 B1 | 3/2001 | Hur | |
| 6,205,855 B1 | 3/2001 | Pfeiffer | |
| 6,206,844 B1 | 3/2001 | Reichel et al. | |
| 6,206,876 B1 | 3/2001 | Levine et al. | |
| 6,210,337 B1 | 4/2001 | Dunham et al. | |
| 6,210,402 B1 | 4/2001 | Olsen et al. | |
| 6,210,403 B1 | 4/2001 | Klicek | |
| 6,214,023 B1 | 4/2001 | Whipple et al. | |
| 6,228,080 B1 | 5/2001 | Gines | |
| 6,231,565 B1 | 5/2001 | Tovey et al. | |
| 6,233,476 B1 | 5/2001 | Strommer et al. | |
| 6,238,366 B1 | 5/2001 | Savage et al. | |
| 6,245,065 B1 | 6/2001 | Panescu et al. | |
| 6,251,110 B1 | 6/2001 | Wampler | |
| 6,252,110 B1 | 6/2001 | Uemura et al. | |
| D444,365 S | 7/2001 | Bass et al. | |
| D445,092 S | 7/2001 | Lee | |
| D445,764 S | 7/2001 | Lee | |
| 6,254,623 B1 | 7/2001 | Haibel, Jr. et al. | |
| 6,257,241 B1 | 7/2001 | Wampler | |
| 6,258,034 B1 | 7/2001 | Hanafy | |
| 6,259,230 B1 | 7/2001 | Chou | |
| 6,267,761 B1 | 7/2001 | Ryan | |
| 6,270,831 B2 | 8/2001 | Kumar et al. | |
| 6,273,852 B1 | 8/2001 | Lehe et al. | |
| 6,274,963 B1 | 8/2001 | Estabrook et al. | |
| 6,277,115 B1 | 8/2001 | Saadat | |
| 6,277,117 B1 | 8/2001 | Tetzlaff et al. | |
| 6,278,218 B1 | 8/2001 | Madan et al. | |
| 6,280,407 B1 | 8/2001 | Manna et al. | |
| 6,283,981 B1 | 9/2001 | Beaupre | |
| 6,287,344 B1 | 9/2001 | Wampler et al. | |
| 6,290,575 B1 | 9/2001 | Shipp | |
| 6,292,700 B1 | 9/2001 | Morrison et al. | |
| 6,299,591 B1 | 10/2001 | Banko | |
| 6,306,131 B1 | 10/2001 | Hareyama et al. | |
| 6,306,157 B1 | 10/2001 | Shchervinsky | |
| 6,309,400 B2 | 10/2001 | Beaupre | |
| 6,311,783 B1 | 11/2001 | Harpell | |
| 6,319,221 B1 | 11/2001 | Savage et al. | |
| 6,325,795 B1 | 12/2001 | Lindemann et al. | |
| 6,325,799 B1 | 12/2001 | Goble | |
| 6,325,811 B1 | 12/2001 | Messerly | |
| 6,328,751 B1 | 12/2001 | Beaupre | |
| 6,332,891 B1 | 12/2001 | Nimes | |
| 6,338,657 B1 | 1/2002 | Harper et al. | |
| 6,340,352 B1 | 1/2002 | Okada et al. | |
| 6,340,878 B1 | 1/2002 | Oglesbee | |
| 6,350,269 B1 | 2/2002 | Shipp et al. | |
| 6,352,532 B1 | 3/2002 | Kramer et al. | |
| 6,358,264 B2 | 3/2002 | Banko | |
| 6,364,888 B1 | 4/2002 | Niemeyer et al. | |
| 6,379,320 B1 | 4/2002 | Lafon et al. | |
| D457,958 S | 5/2002 | Dycus et al. | |
| 6,383,194 B1 | 5/2002 | Pothula | |
| 6,384,690 B1 | 5/2002 | Wilhelmsson et al. | |
| 6,387,109 B1 | 5/2002 | Davison et al. | |
| 6,388,657 B1 | 5/2002 | Natoli | |
| 6,391,026 B1 | 5/2002 | Hung et al. | |
| 6,391,042 B1 | 5/2002 | Cimino | |
| 6,398,779 B1 | 6/2002 | Buysse et al. | |
| 6,402,743 B1 | 6/2002 | Orszulak et al. | |
| 6,402,748 B1 | 6/2002 | Schoenman et al. | |
| 6,405,733 B1 | 6/2002 | Fogarty et al. | |
| 6,409,722 B1 | 6/2002 | Hoey et al. | |
| H2037 H | 7/2002 | Yates et al. | |
| 6,416,486 B1 | 7/2002 | Wampler | |
| 6,419,675 B1 | 7/2002 | Gallo, Sr. | |
| 6,423,073 B2 | 7/2002 | Bowman | |
| 6,423,082 B1 | 7/2002 | Houser et al. | |
| 6,425,906 B1 | 7/2002 | Young et al. | |
| 6,428,538 B1 | 8/2002 | Blewett et al. | |
| 6,428,539 B1 | 8/2002 | Baxter et al. | |
| 6,430,446 B1 | 8/2002 | Knowlton | |
| 6,432,118 B1 | 8/2002 | Messerly | |
| 6,436,114 B1 | 8/2002 | Novak et al. | |
| 6,436,115 B1 | 8/2002 | Beaupre | |
| 6,440,062 B1 | 8/2002 | Ouchi | |
| 6,443,968 B1 | 9/2002 | Holthaus et al. | |
| 6,443,969 B1 | 9/2002 | Novak et al. | |
| 6,449,006 B1 | 9/2002 | Shipp | |
| 6,454,781 B1 | 9/2002 | Witt et al. | |
| 6,454,782 B1 | 9/2002 | Schwemberger | |
| 6,458,128 B1 | 10/2002 | Schulze | |

(56) References Cited

U.S. PATENT DOCUMENTS

| | | |
|---|---|---|
| 6,458,142 B1 | 10/2002 | Faller et al. |
| 6,464,689 B1 | 10/2002 | Qin et al. |
| 6,464,702 B2 | 10/2002 | Schulze et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 * | 9/2004 | Araki ............... C09D 127/18 427/385.5 |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |

(56) References Cited

U.S. PATENT DOCUMENTS

| | | |
|---|---|---|
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |

(56) References Cited

U.S. PATENT DOCUMENTS

| | | |
|---|---|---|
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |

(56) References Cited

U.S. PATENT DOCUMENTS

| | | |
|---|---|---|
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,871,392 B2 | 1/2011 | Sartor |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,323 B2 | 1/2012 | Buysse et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,415 B2 | 7/2012 | Francischelli |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |

(56) References Cited

U.S. PATENT DOCUMENTS

| | | |
|---|---|---|
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,880 B2 | 1/2013 | Messerly et al. |
| 8,348,967 B2 | 1/2013 | Stulen |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,640,788 B2 | 2/2014 | Dachs, II et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,659,208 B1 | 2/2014 | Rose et al. |

(56) References Cited

U.S. PATENT DOCUMENTS

| | | |
|---|---|---|
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,023,071 B2 | 5/2015 | Miller et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,147,965 B2 | 9/2015 | Lee |

(56) References Cited

U.S. PATENT DOCUMENTS

| | | |
|---|---|---|
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,179,912 B2 | 11/2015 | Yates et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,232 B2 | 6/2016 | Hunt et al. |
| 9,375,267 B2 | 6/2016 | Kerr et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,486,236 B2 | 11/2016 | Price et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |

(56) References Cited

U.S. PATENT DOCUMENTS

| | | |
|---|---|---|
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,907,563 B2 | 3/2018 | Germain et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,022,567 B2 | 7/2018 | Messerly et al. |
| 10,022,568 B2 | 7/2018 | Messerly et al. |
| 10,028,786 B2 | 7/2018 | Mucilli et al. |
| 10,034,684 B2 | 7/2018 | Weisenburgh, II |
| 10,034,685 B2 | 7/2018 | Boudreaux |
| 10,034,704 B2 | 7/2018 | Asher et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0100652 A1* | 5/2006 | Beaupre ......... A61B 17/320092 606/169 |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |

(56) References Cited

U.S. PATENT DOCUMENTS

| | | |
|---|---|---|
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0234711 A1* | 9/2008 | Houser .......... A61B 17/320068 606/169 |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0048537 A1* | 2/2009 | Lydon .................. A61L 29/041 600/585 |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0036370 A1 | 2/2010 | Mirel et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0158307 A1 | 6/2010 | Kubota et al. |
| 2010/0168741 A1 | 7/2010 | Sanai et al. |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0274278 A1 | 10/2010 | Fleenor et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0087220 A1 | 4/2011 | Felder et al. |
| 2011/0125151 A1 | 5/2011 | Strauss et al. |
| 2011/0196400 A1* | 8/2011 | Robertson ........ A61B 17/22004 606/169 |
| 2011/0276049 A1 | 11/2011 | Gerhardt |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0059289 A1 | 3/2012 | Nield et al. |
| 2012/0071863 A1 | 3/2012 | Lee et al. |
| 2012/0078139 A1 | 3/2012 | Aldridge et al. |
| 2012/0078244 A1 | 3/2012 | Worrell et al. |
| 2012/0101495 A1 | 4/2012 | Young et al. |
| 2012/0109186 A1 | 5/2012 | Parrott et al. |
| 2012/0116265 A1 | 5/2012 | Houser et al. |
| 2012/0143211 A1 | 6/2012 | Kish |
| 2012/0143233 A1 | 6/2012 | Sinelnikov |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0103065 A1 | 4/2013 | Timm et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0217967 A1 | 8/2013 | Mohr et al. |
| 2013/0253256 A1 | 9/2013 | Griffith et al. |

(56) References Cited

U.S. PATENT DOCUMENTS

| | | |
|---|---|---|
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0081299 A1 | 3/2014 | Dietz et al. |
| 2014/0114327 A1 | 4/2014 | Boudreaux et al. |
| 2014/0121569 A1 | 5/2014 | Schafer et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0257284 A1 | 9/2014 | Artale |
| 2014/0276970 A1 | 9/2014 | Messerly et al. |
| 2014/0330271 A1 | 11/2014 | Dietz et al. |
| 2014/0371735 A1 | 12/2014 | Long |
| 2015/0080876 A1 | 3/2015 | Worrell et al. |
| 2015/0088178 A1 | 3/2015 | Stulen et al. |
| 2015/0112335 A1 | 4/2015 | Boudreaux et al. |
| 2015/0148830 A1 | 5/2015 | Stulen et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182276 A1 | 7/2015 | Wiener et al. |
| 2015/0182277 A1 | 7/2015 | Wiener et al. |
| 2015/0230853 A1 | 8/2015 | Johnson et al. |
| 2015/0230861 A1 | 8/2015 | Woloszko et al. |
| 2015/0250495 A1 | 9/2015 | Robertson et al. |
| 2015/0257780 A1 | 9/2015 | Houser |
| 2015/0272602 A1 | 10/2015 | Boudreaux et al. |
| 2015/0272659 A1 | 10/2015 | Boudreaux et al. |
| 2015/0272660 A1 | 10/2015 | Boudreaux et al. |
| 2015/0340586 A1 | 11/2015 | Wiener et al. |
| 2016/0030076 A1 | 2/2016 | Faller et al. |
| 2016/0045248 A1 | 2/2016 | Unger et al. |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0144204 A1 | 5/2016 | Akagane |
| 2016/0157927 A1 | 6/2016 | Corbett et al. |
| 2016/0175024 A1 | 6/2016 | Yates et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0206342 A1 | 7/2016 | Robertson et al. |
| 2016/0213395 A1 | 7/2016 | Anim |
| 2016/0228171 A1 | 8/2016 | Boudreaux |
| 2016/0262786 A1 | 9/2016 | Madan et al. |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317217 A1 | 11/2016 | Batross et al. |
| 2016/0338726 A1 | 11/2016 | Stulen et al. |
| 2016/0346001 A1 | 12/2016 | Vakharia et al. |
| 2016/0367273 A1 | 12/2016 | Robertson et al. |
| 2016/0367281 A1 | 12/2016 | Gee et al. |
| 2016/0374708 A1 | 12/2016 | Wiener et al. |
| 2016/0374709 A1 | 12/2016 | Timm et al. |
| 2016/0374712 A1 | 12/2016 | Stulen et al. |
| 2017/0000512 A1 | 1/2017 | Conlon et al. |
| 2017/0000513 A1 | 1/2017 | Conlon et al. |
| 2017/0000541 A1 | 1/2017 | Yates et al. |
| 2017/0056056 A1 | 3/2017 | Wiener et al. |
| 2017/0056058 A1 | 3/2017 | Voegele et al. |
| 2017/0086876 A1 | 3/2017 | Wiener et al. |
| 2017/0086906 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0090507 A1 | 3/2017 | Wiener et al. |
| 2017/0095267 A1 | 4/2017 | Messerly et al. |
| 2017/0105757 A1 | 4/2017 | Weir et al. |
| 2017/0105791 A1 | 4/2017 | Yates et al. |
| 2017/0106786 A1 | 4/2017 | Scheib et al. |
| 2017/0143371 A1 | 5/2017 | Witt et al. |
| 2017/0143877 A1 | 5/2017 | Witt et al. |
| 2017/0164972 A1 | 6/2017 | Johnson et al. |
| 2017/0172700 A1 | 6/2017 | Denzinger et al. |
| 2017/0189095 A1 | 7/2017 | Danziger et al. |
| 2017/0189096 A1 | 7/2017 | Danziger et al. |
| 2017/0189101 A1 | 7/2017 | Yates et al. |
| 2017/0196586 A1 | 7/2017 | Witt et al. |
| 2017/0196587 A1 | 7/2017 | Witt et al. |
| 2017/0202570 A1 | 7/2017 | Shelton, IV et al. |
| 2017/0202571 A1 | 7/2017 | Shelton, IV et al. |
| 2017/0202572 A1 | 7/2017 | Shelton, IV et al. |
| 2017/0202573 A1 | 7/2017 | Witt et al. |
| 2017/0202591 A1 | 7/2017 | Shelton, IV et al. |
| 2017/0202592 A1 | 7/2017 | Shelton, IV et al. |
| 2017/0202593 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2018/0014845 A1 | 1/2018 | Dannaher |
| 2018/0014846 A1 | 1/2018 | Rhee et al. |
| 2018/0014848 A1 | 1/2018 | Messerly et al. |
| 2018/0042634 A1 | 2/2018 | Conlon et al. |
| 2018/0049767 A1 | 2/2018 | Gee et al. |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0056095 A1 | 3/2018 | Messerly et al. |
| 2018/0078268 A1 | 3/2018 | Messerly et al. |
| 2018/0092660 A1 | 4/2018 | Houser et al. |
| 2018/0146975 A1 | 5/2018 | Zhang |
| 2018/0168680 A1 | 6/2018 | Houser et al. |
| 2018/0199957 A1 | 7/2018 | Robertson et al. |
| 2018/0206881 A1 | 7/2018 | Price et al. |
| 2018/0263653 A1 | 9/2018 | Witt et al. |

FOREIGN PATENT DOCUMENTS

| | | |
|---|---|---|
| CN | 1233944 A | 11/1999 |
| CN | 1253485 A | 5/2000 |
| CN | 2460047 Y | 11/2001 |
| CN | 1634601 A | 7/2005 |

(56) References Cited

FOREIGN PATENT DOCUMENTS

| | | | |
|---|---|---|---|
| CN | 1640365 A | 7/2005 |
| CN | 1694649 A | 11/2005 |
| CN | 1775323 A | 5/2006 |
| CN | 1922563 A | 2/2007 |
| CN | 2868227 Y | 2/2007 |
| CN | 1951333 A | 4/2007 |
| CN | 101035482 A | 9/2007 |
| CN | 101040799 A | 9/2007 |
| CN | 101396300 A | 4/2009 |
| CN | 101467917 A | 7/2009 |
| CN | 101674782 A | 3/2010 |
| CN | 101883531 A | 11/2010 |
| CN | 102160045 A | 8/2011 |
| CN | 202027624 U | 11/2011 |
| CN | 102834069 A | 12/2012 |
| CN | 101313865 B | 1/2013 |
| DE | 3904558 A1 | 8/1990 |
| DE | 9210327 U1 | 11/1992 |
| DE | 4300307 A1 | 7/1994 |
| DE | 4323585 A1 | 1/1995 |
| DE | 19608716 C1 | 4/1997 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0342448 A1 | 11/1989 |
| EP | 0443256 A1 | 8/1991 |
| EP | 0456470 A1 | 11/1991 |
| EP | 0238667 B1 | 2/1993 |
| EP | 0340803 B1 | 8/1993 |
| EP | 0598976 A2 | 6/1994 |
| EP | 0630612 A1 | 12/1994 |
| EP | 0424685 B1 | 5/1995 |
| EP | 0677275 A2 | 10/1995 |
| EP | 0482195 B1 | 1/1996 |
| EP | 0695535 A1 | 2/1996 |
| EP | 0705571 A1 | 4/1996 |
| EP | 0741996 B1 | 11/1996 |
| EP | 0612570 B1 | 6/1997 |
| EP | 0557806 B1 | 5/1998 |
| EP | 0640317 B1 | 9/1999 |
| EP | 1108394 A2 | 6/2001 |
| EP | 1138264 A1 | 10/2001 |
| EP | 0908148 B1 | 1/2002 |
| EP | 1229515 A2 | 8/2002 |
| EP | 0722696 B1 | 12/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1293172 B1 | 4/2006 |
| EP | 0875209 B1 | 5/2006 |
| EP | 1433425 B1 | 6/2006 |
| EP | 1256323 B1 | 8/2006 |
| EP | 1698289 A2 | 9/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1815950 A1 | 8/2007 |
| EP | 1839599 A1 | 10/2007 |
| EP | 1844720 A1 | 10/2007 |
| EP | 1862133 A1 | 12/2007 |
| EP | 1875875 A1 | 1/2008 |
| EP | 1878399 A1 | 1/2008 |
| EP | 1915953 A1 | 4/2008 |
| EP | 1532933 B1 | 5/2008 |
| EP | 1199045 B1 | 6/2008 |
| EP | 1707143 B1 | 6/2008 |
| EP | 1943957 A2 | 7/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1477104 B1 | 1/2009 |
| EP | 2014218 A2 | 1/2009 |
| EP | 1849424 B1 | 4/2009 |
| EP | 2042112 A2 | 4/2009 |
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 2106758 A1 | 10/2009 |
| EP | 2111813 A1 | 10/2009 |
| EP | 2131760 A1 | 12/2009 |
| EP | 1769766 B1 | 2/2010 |
| EP | 2151204 A1 | 2/2010 |
| EP | 2153791 A1 | 2/2010 |
| EP | 2200145 A1 | 6/2010 |
| EP | 1214913 B1 | 7/2010 |
| EP | 2238938 A1 | 10/2010 |
| EP | 2243439 A1 | 10/2010 |
| EP | 2298154 A2 | 3/2011 |
| EP | 2305144 A1 | 4/2011 |
| EP | 1510178 B1 | 6/2011 |
| EP | 1946708 B1 | 6/2011 |
| EP | 2335630 A1 | 6/2011 |
| EP | 1502551 B1 | 7/2011 |
| EP | 1728475 B1 | 8/2011 |
| EP | 2353518 A1 | 8/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 1586275 B1 | 5/2013 |
| EP | 1616529 B1 | 9/2013 |
| EP | 1997438 B1 | 11/2013 |
| EP | 2508143 B1 | 2/2014 |
| EP | 2583633 B1 | 10/2014 |
| EP | 2113210 B1 | 3/2016 |
| EP | 2510891 B1 | 6/2016 |
| EP | 2227155 B1 | 7/2016 |
| EP | 2859858 B1 | 12/2016 |
| ES | 2115068 T3 | 6/1998 |
| GB | 1482943 A | 8/1977 |
| GB | 2032221 A | 4/1980 |
| GB | 2317566 A | 4/1998 |
| GB | 2379878 B | 11/2004 |
| GB | 2425480 A | 11/2006 |
| GB | 2472216 A | 2/2011 |
| GB | 2447767 B | 8/2011 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |

(56) References Cited

FOREIGN PATENT DOCUMENTS

| | | |
|---|---|---|
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04150847 A | 5/1992 |
| JP | H04152942 A | 5/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H06217988 A | 8/1994 |
| JP | H06507081 A | 8/1994 |
| JP | H 07500514 A | 1/1995 |
| JP | H07508910 A | 10/1995 |
| JP | H07308323 A | 11/1995 |
| JP | H0824266 A | 1/1996 |
| JP | H08229050 A | 9/1996 |
| JP | H08275951 A | 10/1996 |
| JP | H08299351 A | 11/1996 |
| JP | H08336544 A | 12/1996 |
| JP | H08336545 A | 12/1996 |
| JP | H09503146 A | 3/1997 |
| JP | H09135553 A | 5/1997 |
| JP | H09140722 A | 6/1997 |
| JP | H105237 A | 1/1998 |
| JP | H10295700 A | 11/1998 |
| JP | H11501543 A | 2/1999 |
| JP | H11128238 A | 5/1999 |
| JP | H11192235 A | 7/1999 |
| JP | H11253451 A | 9/1999 |
| JP | H11318918 A | 11/1999 |
| JP | 2000041991 A | 2/2000 |
| JP | 2000070279 A | 3/2000 |
| JP | 2000210299 A | 8/2000 |
| JP | 2000271145 A | 10/2000 |
| JP | 2000287987 A | 10/2000 |
| JP | 2001029353 A | 2/2001 |
| JP | 2001502216 A | 2/2001 |
| JP | 2001309925 A | 11/2001 |
| JP | 2002177295 A | 6/2002 |
| JP | 2002186901 A | 7/2002 |
| JP | 2002204808 A | 7/2002 |
| JP | 2002238919 A | 8/2002 |
| JP | 2002263579 A | 9/2002 |
| JP | 2002301086 A | 10/2002 |
| JP | 2002306504 A | 10/2002 |
| JP | 2002330977 A | 11/2002 |
| JP | 2002542690 A | 12/2002 |
| JP | 2003000612 A | 1/2003 |
| JP | 2003010201 A | 1/2003 |
| JP | 2003510158 A | 3/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003530921 A | 10/2003 |
| JP | 2003310627 A | 11/2003 |
| JP | 2003339730 A | 12/2003 |
| JP | 2004129871 A | 4/2004 |
| JP | 2004147701 A | 5/2004 |
| JP | 2005027026 A | 1/2005 |
| JP | 2005040222 A | 2/2005 |
| JP | 2005066316 A | 3/2005 |
| JP | 2005074088 A | 3/2005 |
| JP | 2005507679 A | 3/2005 |
| JP | 2005534451 A | 11/2005 |
| JP | 2006006410 A | 1/2006 |
| JP | 2006512149 A | 4/2006 |
| JP | 2006116194 A | 5/2006 |
| JP | 2006158525 A | 6/2006 |
| JP | 2006217716 A | 8/2006 |
| JP | 2006218296 A | 8/2006 |
| JP | 2006288431 A | 10/2006 |
| JP | 2007050181 A | 3/2007 |
| JP | 2007-524459 A | 8/2007 |
| JP | 2007229454 A | 9/2007 |
| JP | 2007527747 A | 10/2007 |
| JP | 2007296369 A | 11/2007 |
| JP | 2008018226 A | 1/2008 |
| JP | 2008036390 A | 2/2008 |
| JP | 2008508065 A | 3/2008 |
| JP | 2008119250 A | 5/2008 |
| JP | 2008515562 A | 5/2008 |
| JP | 2008521503 A | 6/2008 |
| JP | D1339835 S | 8/2008 |
| JP | 2008212679 A | 9/2008 |
| JP | 2008536562 A | 9/2008 |
| JP | 2008284374 A | 11/2008 |
| JP | 2009511206 A | 3/2009 |
| JP | 2009082711 A | 4/2009 |
| JP | 2009517181 A | 4/2009 |
| JP | 4262923 B2 | 5/2009 |
| JP | 2009523567 A | 6/2009 |
| JP | 2009148557 A | 7/2009 |
| JP | 2009236177 A | 10/2009 |
| JP | 2009254819 A | 11/2009 |
| JP | 2010000336 A | 1/2010 |
| JP | 2010009686 A | 1/2010 |
| JP | 2010514923 A | 5/2010 |
| JP | 2010121865 A | 6/2010 |
| JP | 2010534522 A | 11/2010 |
| JP | 2010540186 A | 12/2010 |
| JP | 2011505198 A | 2/2011 |
| JP | 2012/075899 A | 4/2012 |
| JP | 2012235658 A | 11/2012 |
| JP | 5208761 B2 | 6/2013 |
| JP | 5714508 B2 | 5/2015 |
| JP | 2015515339 A | 5/2015 |
| JP | 5836543 B1 | 12/2015 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2304934 C2 | 8/2007 |
| RU | 2405603 C1 | 12/2010 |
| SU | 850068 A1 | 7/1981 |
| WO | WO-8103272 A1 | 11/1981 |
| WO | WO-9222259 A2 | 12/1992 |
| WO | WO-9307817 A1 | 4/1993 |
| WO | WO-9308757 A1 | 5/1993 |
| WO | WO-9314708 A1 | 8/1993 |
| WO | WO-9316646 A1 | 9/1993 |
| WO | WO-9320877 A1 | 10/1993 |
| WO | WO-9322973 A1 | 11/1993 |
| WO | WO-9400059 A1 | 1/1994 |
| WO | WO-9421183 A1 | 9/1994 |
| WO | WO-9424949 A1 | 11/1994 |
| WO | WO-9509572 A1 | 4/1995 |
| WO | WO-9510978 A1 | 4/1995 |
| WO | WO-9534259 A1 | 12/1995 |
| WO | WO-9630885 A1 | 10/1996 |
| WO | WO-9635382 A1 | 11/1996 |
| WO | WO-9639086 A1 | 12/1996 |
| WO | WO-9710764 A1 | 3/1997 |
| WO | WO-9800069 A1 | 1/1998 |
| WO | WO-9816156 A1 | 4/1998 |
| WO | WO-9826739 A1 | 6/1998 |
| WO | WO-9835621 A1 | 8/1998 |
| WO | WO-9837815 A1 | 9/1998 |
| WO | WO-9840020 A1 | 9/1998 |
| WO | WO-9847436 A1 | 10/1998 |
| WO | WO-9857588 A1 | 12/1998 |
| WO | WO-9920213 A1 | 4/1999 |
| WO | WO-9923960 A1 | 5/1999 |
| WO | WO-9940857 A1 | 8/1999 |
| WO | WO-9940861 A1 | 8/1999 |
| WO | WO-9952489 A1 | 10/1999 |
| WO | WO-0024330 A1 | 5/2000 |
| WO | WO-0024331 A1 | 5/2000 |

(56) References Cited

FOREIGN PATENT DOCUMENTS

| | | |
|---|---|---|
| WO | WO-0025691 A1 | 5/2000 |
| WO | WO-0064358 A2 | 11/2000 |
| WO | WO-0074585 A2 | 12/2000 |
| WO | WO-0124713 A1 | 4/2001 |
| WO | WO-0128444 A1 | 4/2001 |
| WO | WO-0154590 A1 | 8/2001 |
| WO | WO-0167970 A1 | 9/2001 |
| WO | WO-0195810 A2 | 12/2001 |
| WO | WO-0224080 A2 | 3/2002 |
| WO | WO-0238057 A1 | 5/2002 |
| WO | WO-02062241 A1 | 8/2002 |
| WO | WO-02080797 A1 | 10/2002 |
| WO | WO-03001986 A2 | 1/2003 |
| WO | WO-03013374 A1 | 2/2003 |
| WO | WO-03020339 A2 | 3/2003 |
| WO | WO-03028541 A2 | 4/2003 |
| WO | WO-03030708 A2 | 4/2003 |
| WO | WO-03068046 A2 | 8/2003 |
| WO | WO-03082133 A1 | 10/2003 |
| WO | WO-2004011037 A2 | 2/2004 |
| WO | WO-2004012615 A1 | 2/2004 |
| WO | WO-2004026104 A2 | 4/2004 |
| WO | WO-2004032754 A2 | 4/2004 |
| WO | WO-2004032762 A1 | 4/2004 |
| WO | WO-2004032763 A2 | 4/2004 |
| WO | WO-2004037095 A2 | 5/2004 |
| WO | WO-2004060141 A2 | 7/2004 |
| WO | WO-2004078051 A2 | 9/2004 |
| WO | WO-2004098426 A1 | 11/2004 |
| WO | WO-2004112618 A2 | 12/2004 |
| WO | WO-2005052959 A2 | 6/2005 |
| WO | WO-2005117735 A1 | 12/2005 |
| WO | WO-2005122917 A1 | 12/2005 |
| WO | WO-2006012797 A1 | 2/2006 |
| WO | WO-2006021269 A1 | 3/2006 |
| WO | WO-2006036706 A1 | 4/2006 |
| WO | WO-2006042210 A2 | 4/2006 |
| WO | WO-2006055166 A2 | 5/2006 |
| WO | WO-2006058223 A2 | 6/2006 |
| WO | WO-2006063199 A2 | 6/2006 |
| WO | WO-2006083988 A1 | 8/2006 |
| WO | WO-2006101661 A2 | 9/2006 |
| WO | WO-2006119139 A2 | 11/2006 |
| WO | WO-2006119376 A2 | 11/2006 |
| WO | WO-2006129465 A1 | 12/2006 |
| WO | WO-2007008703 A2 | 1/2007 |
| WO | WO-2007008710 A2 | 1/2007 |
| WO | WO-2007038538 A1 | 4/2007 |
| WO | WO-2007040818 A1 | 4/2007 |
| WO | WO-2007047380 A2 | 4/2007 |
| WO | WO-2007047531 A2 | 4/2007 |
| WO | WO-2007056590 A1 | 5/2007 |
| WO | WO-2007087272 A2 | 8/2007 |
| WO | WO-2007089724 A2 | 8/2007 |
| WO | WO-2007143665 A2 | 12/2007 |
| WO | WO-2008016886 A2 | 2/2008 |
| WO | WO-2008020964 A2 | 2/2008 |
| WO | WO-2008042021 A1 | 4/2008 |
| WO | WO-2008045348 A2 | 4/2008 |
| WO | WO-2008049084 A2 | 4/2008 |
| WO | WO-2008051764 A2 | 5/2008 |
| WO | WO-2008089174 A2 | 7/2008 |
| WO | WO-2008099529 A1 | 8/2008 |
| WO | WO-2008101356 A1 | 8/2008 |
| WO | WO-2008118709 A1 | 10/2008 |
| WO | WO-2008130793 A1 | 10/2008 |
| WO | WO-2009010565 A1 | 1/2009 |
| WO | WO-2009018067 A1 | 2/2009 |
| WO | WO-2009018406 A2 | 2/2009 |
| WO | WO-2009022614 A1 | 2/2009 |
| WO | WO-2009027065 A1 | 3/2009 |
| WO | WO-2009036818 A1 | 3/2009 |
| WO | WO-2009039179 A1 | 3/2009 |
| WO | WO-2009046234 A2 | 4/2009 |
| WO | WO-2009059741 A1 | 5/2009 |
| WO | WO-2009073402 A2 | 6/2009 |
| WO | WO-2009082477 A2 | 7/2009 |
| WO | WO-2009088550 A2 | 7/2009 |
| WO | WO-2009120992 A2 | 10/2009 |
| WO | WO-2009141616 A1 | 11/2009 |
| WO | WO-2009149234 A1 | 12/2009 |
| WO | WO-2010017149 A1 | 2/2010 |
| WO | WO-2010017266 A1 | 2/2010 |
| WO | WO-2010068783 A1 | 6/2010 |
| WO | WO-2010104755 A1 | 9/2010 |
| WO | WO-2011008672 A2 | 1/2011 |
| WO | WO-2011/044338 A2 | 4/2011 |
| WO | WO-2011052939 A2 | 5/2011 |
| WO | WO-2011060031 A1 | 5/2011 |
| WO | WO-2011084768 A1 | 7/2011 |
| WO | WO-2011089717 A1 | 7/2011 |
| WO | WO-2011100321 A2 | 8/2011 |
| WO | WO-2011144911 A1 | 11/2011 |
| WO | WO-2012044597 A1 | 4/2012 |
| WO | WO-2012044606 A2 | 4/2012 |
| WO | WO-2012061722 A2 | 5/2012 |
| WO | WO-2012128362 A1 | 9/2012 |
| WO | WO-2012135705 A1 | 10/2012 |
| WO | WO-2012135721 A1 | 10/2012 |
| WO | WO-2012166510 A1 | 12/2012 |
| WO | WO-2013018934 A1 | 2/2013 |
| WO | WO-2013034629 A1 | 3/2013 |
| WO | WO-2013062978 A2 | 5/2013 |
| WO | WO-2013102602 A2 | 7/2013 |
| WO | WO-2013154157 A1 | 10/2013 |
| WO | WO-2014092108 A1 | 6/2014 |
| WO | WO-2015197395 A8 | 12/2015 |
| WO | WO-2016009921 A1 | 1/2016 |

OTHER PUBLICATIONS

AST Products, Inc., "Principles of Video Contact Angle Analysis," 20 pages, (2006).

Campbell et al, "Thermal Imaging in Surgery," p. 19-3, in Medical Infrared Imaging, N. A. Diakides and J. D. Bronzino, Eds. (2008).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Heat-induced changes in the mechanics of a collagenous tissue: pseudoelastic behavior at 37° C.," Journal of Biomechanics, 31, pp. 211-216 (1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Covidien 501(k) Summary Sonicision, dated Feb. 24, 2011 (7 pages).

Covidien Brochure, [Value Analysis Brief], LigaSure Advance™ Pistol Grip, dated Rev. Apr. 2010 (7 pages).

Covidien Brochure, LigaSure Atlas™ Hand Switching Instruments, dated Dec. 2008 (2 pages).

Covidien Brochure, LigaSure Impact™ Instrument LF4318, dated Feb. 2013 (3 pages).

Covidien Brochure, The LigaSure Precise™ Instrument, dated Mar. 2011 (2 pages).

Covidien Brochure, The LigaSure™ 5 mm Blunt Tip Sealer/Divider Family, dated Apr. 2013 (2 pages).

Douglas, S.C. "Introduction to Adaptive Filter". Digital Signal Processing Handbook. Ed. Vijay K. Madisetti and Douglas B. Williams. Boca Raton: CRC Press LLC, 1999.

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

F. A. Duck, "Optical Properties of Tissue Including Ultraviolet and Infrared Radiation," pp. 43-71 in Physical Properties of Tissue (1990).

(56) References Cited

OTHER PUBLICATIONS

Fowler, K.R., "A Programmable, Arbitrary Waveform Electrosurgical Device," IEEE Engineering in Medicine and Biology Society 10th Annual International Conference, pp. 1324, 1325 (1988).
Gerhard, Glen C., "Surgical Electrotechnology: Quo Vadis?," IEEE Transactions on Biomedical Engineering, vol. BME-31, No. 12, pp. 787-792, Dec. 1984.
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Glaser and Subak-Sharpe,Integrated Circuit Engineering, Addison-Wesley Publishing, Reading, MA (1979). (book—not attached).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Graff, K.F., "Elastic Wave Propagation in a Curved Sonic Transmission Line," IEEE Transactions on Sonics and Ultrasonics, SU-17(1), 1-6 (1970).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
htlp://www.4-traders.com/JOHNSON-JOHNSON-4832/news/Johnson-Johnson-Ethicon-E . . . .
http://www.apicalinstr.com/generators.htm.
http://www.dotmed.com/listing/electrosurical-unit/ethicon/ultracision-g110-/1466724.
http://www.medicalexpo.com/medical-manufacturer/electrosurgical-generator-6951.html.
http://www.megadyne.com/es_generator.php.
http://www.valleylab.com/product/es/generators/index.html.
http:/www.ethicon.com/gb-en/healthcare-professionals/products/energy-devices/capital//ge . . . .
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Humphrey, J.D., "Continuum Thermomechanics and the Clinical Treatment of Disease and Injury," Appl. Mech. Rev., vol. 56, No. 2 pp. 231-260 (Mar. 2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).

Jang, J. et al. "Neuro-fuzzy and Soft Computing." Prentice Hall, 1997, pp. 13-89, 199-293, 335-393, 453-496, 535-549.
Kurt Gieck & Reiner Gieck, Engineering Formulas § Z.7 (7th ed. 1997).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Lee et al., "A multi-sample denaturation temperature tester for collagenous biomaterials," Med. Eng. Phy., vol. 17, No. 2, pp. 115-121 (Mar. 1995).
Leonard I. Malis, M.D., "The Value of Irrigation During Bipolar Coagulation," 1989.
Lim et al., "A Review of Mechanism Used in Laparoscopic Surgical Instruments," Mechanism and Machine Theory, vol. 38, pp. 1133-1147, (2003).
Makarov, S. N., Ochmann, M., Desinger, K, "The longitudinal vibration response of a curved fiber used for laser ultrasound surgical therapy," Journal of the Acoustical Society of America 102, 1191-1199 (1997).
Moran et al., "Thermally Induced Shrinkage of Joint Capsule," Clinical Orthopaedics and Related Research, No. 281, pp. 248-255 (Dec. 2000).
Morley, L. S. D., "Elastic Waves in a Naturally Curved Rod," Quarterly Journal of Mechanics and Applied Mathematics, 14: 155-172 (1961).
National Semiconductors Temperature Sensor Handbook—http://www.national.com/appinfo/tempsensors/files/temphb.pdf; accessed online: Apr. 1, 2011.
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Technology Overview, printed from www.harmonicscalpel.com, Internet site, website accessed on Jun. 13, 2007, (3 pages).
Wall et al., "Thermal modification of collagen," J Shoulder Elbow Surg, No. 8, pp. 339-344 (Jul./Aug. 1999).
Walsh, S. J., White, R. G., "Vibrational Power Transmission in Curved Beams," Journal of Sound and Vibration, 233(3), 455-488 (2000).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.

* cited by examiner

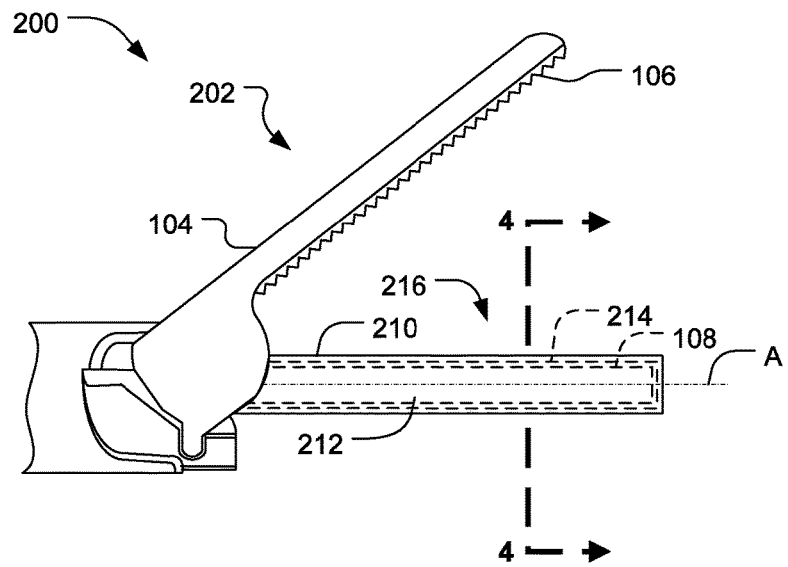
FIG. 3
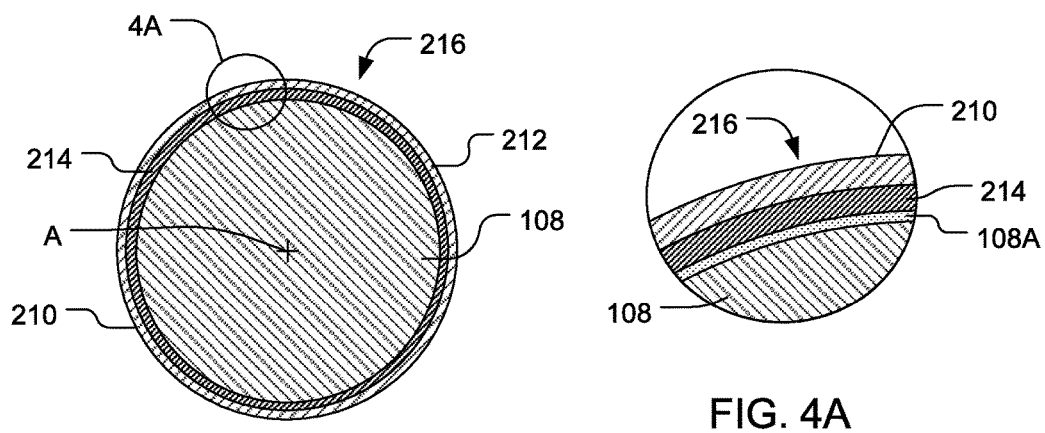
FIG. 4
FIG. 4A

ULTRASONIC SURGICAL BLADES

CROSS REFERENCE TO RELATED APPLICATIONS

This application is a continuation application claiming priority under 35 U.S.C. § 120 to U.S. patent application Ser. No. 15/477,861, entitled ULTRASONIC SURGICAL BLADES, filed Apr. 3, 2017, now U.S. Patent Application Publication No. 2017/0202573, which is a continuation application claiming priority under 35 U.S.C. § 120 to U.S. patent application Ser. No. 12/274,884, entitled ULTRASONIC SURGICAL BLADES, filed Nov. 20, 2008, now U.S. Patent Application Publication No. 2009/0143806, which claims the benefit under Title 35, United States Code § 119(e), of U.S. Provisional Patent Application Ser. No. 61/004,961, filed Nov. 30, 2007, entitled ULTRASONIC SURGICAL BLADES, the entire disclosures of which are hereby incorporated by reference herein.

BACKGROUND

The present disclosure is generally directed to ultrasonic surgical blades employed in ultrasonic instruments. At present, ultrasonic instruments are used in open as well as minimally invasive surgical procedures, including endoscopic and laparoscopic surgical procedures where an end-effector portion of the ultrasonic instrument is passed through a trocar to reach the surgical site. Due, in part, to the rising popularity of minimally invasive surgical procedures, ultrasonic instruments are increasingly being used for the safe and effective treatment of many medical conditions. The operation of instruments employing an ultrasonic transducer in this context is well known in the art and it will not be repeated herein for the sake of conciseness and brevity. Stated briefly, an ultrasonic transducer excited by an electrical generator produces mechanical vibrations at ultrasonic frequencies, which are transmitted longitudinally through a transmission component or waveguide to an end-effector. The mechanical vibrations induce longitudinal, transverse, or torsional vibratory movement to the end-effector relative to the transmission component. The vibratory movement of the end-effector generates localized heat within adjacent tissue, facilitating both cutting and coagulating of tissue at the same time. Accordingly, the ultrasonic vibrations, when transmitted to organic tissue at suitable energy levels using a suitable end-effector, may be used to cut, dissect, separate, lift, transect, elevate, coagulate or cauterize tissue, or to separate or scrape muscle tissue away from bone with or without the assistance of a clamping assembly.

It is generally accepted that ultrasonic instruments, and particularly ultrasonic instruments comprising contact ultrasonic elements, provide certain advantages over other surgical instruments. Among these advantages is that the ultrasonic mechanical vibrations can cut and coagulate tissue at the same time using relatively lower temperatures than conventional cutting and cauterizing surgical instruments. The nature of ultrasonic instruments lend themselves to multiple applications and a variety of end-effectors may be designed to perform numerous functions.

Ultrasonic instruments may be classified into single-element end-effector devices and multiple-element end-effector devices. Single-element end-effector devices include instruments such as blades, scalpels, hooks, and/or ball coagulators. Although generally, these types of end-effectors are formed of solid materials suitable for propagating ultrasonic waves, there also exist end-effectors with a hollow core to deliver a fluid stream or provide a suction channel. Multiple-element end-effectors include the single-element end-effector—blade—operatively coupled to a clamping mechanism for pressing or clamping tissue between the blade and the clamping mechanism. Multiple-element end-effectors include clamping scalpels, clamping coagulators or any combination of a clamping mechanism and a single-element end-effector. Clamping end-effectors are particularly useful when a substantial amount of pressure is necessary to effectively couple ultrasonic energy from the blade to the tissue. Clamping end-effectors apply a compressive or biasing force to the tissue to promote faster cutting and coagulation of tissue, particularly loose and unsupported tissue.

With this general background in mind, it should be noted that surgical environments where ultrasonic instruments are employed can be particularly harsh due to the mechanical vibratory forces applied to the end-effector, the resulting thermal effects, and the general caustic conditions present at the surgical site. For example, in use, the end-effector comes into contact with surgical matter, which includes coagulants, proteins, blood, tissue particles, and other constituent fluids. Over time, the surgical matter tends to desiccate and adhere to the outer (e.g., external) surface of the end-effector. This buildup of surgical matter tends to reduce the performance of the end-effector by reducing the ability of the end-effector to cut and/or coagulate tissue and increasing the impedance at the end-effector/tissue interface. To compensate for the increase in interface impedance, the generator supplies increasing amounts of power to the end-effector to continue transecting tissue until the power delivered by the generator exceeds a predetermined threshold at which time the generator shuts down or goes into "lockout." Lockout is a condition where the impedance of the end-effector is so high that the generator is unable to provide meaningful amounts of power to the tissue. Generator lockout is an undesirable result that occurs when the generator is unable to supply adequate power to the end-effector to complete a transection under the increased interface impedance condition. The completion of a transection is indicated to the user by the visual separation of the tissue from the device end-effector. When the generator goes into lockout, the surgical procedure is interrupted. Therefore, generator lockout results in increased cutting and transection times, or worse, down time during the surgical procedure.

Accordingly, there is a need for an end-effector with a suitable coating or suitable combination of a coating and a surface treatment to protect the end-effector from harsh surgical environments. In this regard, the suitable coating or suitable combination of a coating and a surface treatment prevents or minimizes buildup of surgical matter on the outer surface of the end-effector, minimizes generator lockout, minimizes power draw, improves pad wear in clamping type end-effectors, and improves the thermal characteristics of the end-effector. There is also needed a process of applying one or more suitable coatings to an outer surface of an end-effector to enable the adhesion of the one or more coatings to the outer surface of the end-effector.

SUMMARY

In one general aspect, the various embodiments are directed to an ultrasonic surgical blade. The ultrasonic surgical blade comprises a body having a proximal end, a distal end, and an outer surface. The distal end is movable relative to a longitudinal axis in accordance with ultrasonic vibrations applied to the proximal end. At least a portion of the outer surface of the body comprises a lubricious coating adhered thereto. The lubricious coating has a coefficient of friction that is less than the coefficient of friction of the outer surface of the body

FIGURES

The novel features of the various embodiments are set forth with particularity in the appended claims. The various embodiments, however, both as to organization and methods of operation, may be best understood by reference to the following description, taken in conjunction with the accompanying drawings as follows.

FIG. 3 illustrates one embodiment of a multi-element end-effector.

FIG. 4 illustrates a cross-sectional view of the ultrasonic blade portion of the multi-element end-effector shown in FIG. 3 taken along line 4-4.

FIG. 4A is an enlarged view of a portion of the cross-sectional portion of one embodiment of the ultrasonic blade portion of the multi-element end-effector shown in FIG. 3.

DESCRIPTION

Figure 1:
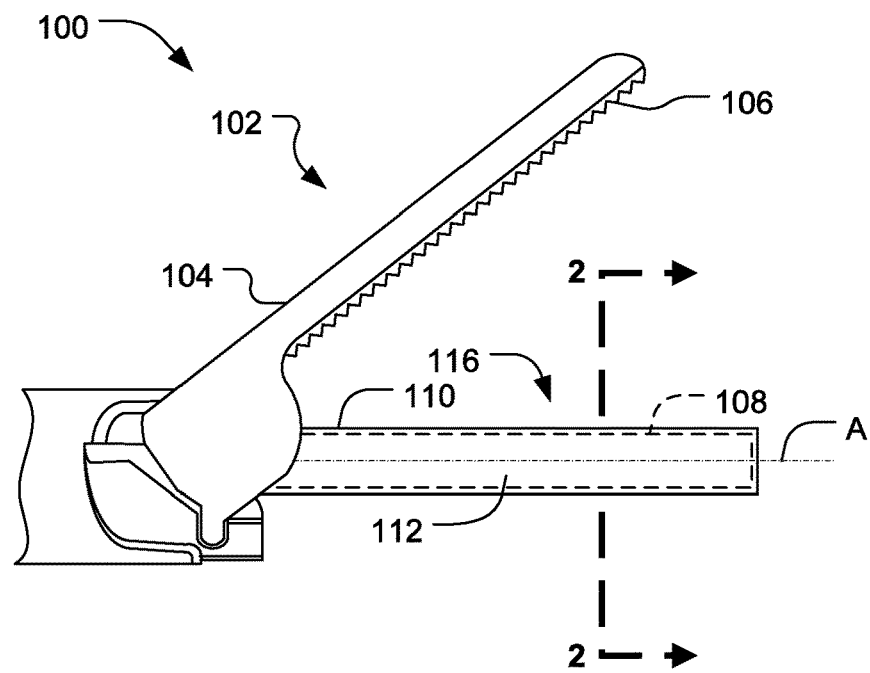
FIG. 1 illustrates one embodiment of a multi-element end-effector.

Before explaining the various embodiments in detail, it should be noted that the embodiments are not limited in application or use to the details of construction and arrangement of parts illustrated in the accompanying drawings and description. The surgical instruments and end-effector configurations disclosed herein are illustrative only and not meant to limit the scope of the appended claims or application thereof. The illustrative embodiments may be implemented or incorporated in other embodiments, variations and modifications, and may be practiced or carried out in various ways. Furthermore, unless otherwise indicated, the terms and expressions employed herein have been chosen for the purpose of describing the illustrative embodiments for the convenience of the reader and are not to limit the scope thereof.

The various embodiments relate, in general, to end-effectors for use in ultrasonic surgical instruments. An ultrasonic surgical instrument generally comprises an ultrasonic transducer, an ultrasonically activated end-effector, and a substantially solid, or hollow, ultrasonic waveguide that connects the ultrasonic transducer to the end-effector. The ultrasonic transducer is contained in a transducing handpiece. The end-effector may be formed of a base material (e.g., body) that is suitable for efficiently transmitting or propagating acoustic waves at ultrasonic frequencies. Thus, the end-effector is an ultrasound-propagating element, which may be coupled to the ultrasonic transducer either directly or by way of the ultrasonic transmission waveguide. Examples of ultrasonic surgical instruments are disclosed in U.S. Pat. Nos. 5,322,055 and 5,954,736 and combinations of ultrasonic end-effectors (e.g., blades) and surgical instruments are disclosed in U.S. Pat. Nos. 6,309,400 B2, 6,278, 218 B1, 6,283,981 B1, and 6,325,811 B1, which are incorporated herein by reference in their entirety. These references provide a suitable general description of ultrasonic instruments and end-effectors. Accordingly, the particular operation of such ultrasonic instruments and end-effectors will not be discussed in detail herein.

More particularly, the embodiments are directed to ultrasonic end-effectors comprising one or more coatings formed as layers of materials, surface treatments, and/or any combination thereof. A suitable coating formed on an outer surface of an ultrasonic end-effector provides a lubricating effect and, therefore, is useful in minimizing adhesion of surgical matter to the outer surface of the end-effector. The lubricating coating also reduces friction between the end-effector and the tissue and thus minimizes the interface impedance between the end-effector and the tissue and reduced the heat buildup in the end-effector. This results in less power being drawn from the ultrasonic generator and an end-effector with a cooler thermal profile that minimizes generator lockout and improves the overall operational stability of the surgical instrument. One skilled in the art would expect that a decrease in average power draw (due, again, to reduced interface impedance) would result in a corresponding increase in the time required to perform surgical procedures such as the cutting and coagulation of a tissue bundle. However, this tradeoff in transection time has not been seen in testing and, in fact, an unexpected decrease in transection times has been consistently obtained. Further investigation has revealed two causes for the unexpected results that heretofore have not been described in the art: (1) the lower coefficient of friction coatings (most coatings presented herein have low friction constituents such as polytetrafluoroethylene generally known as TEFLON® and referred to hereinbelow as PTFE) do not adhere to tissue and thus the tissue releases from the blade (the indication of a completed transection) more uniformly and more quickly than a comparable uncoated blade and (2) the lower coefficient of friction and, therefore, interface impedance, results in a lower average power draw and therefore far fewer incidents of generator lockout. In some embodiments, the transection time has been reduced by about 34% by virtue of the first listed cause. In some embodiments, lengths of thick, tough tissue (uterine broad ligament, for example) have been transected in successive applications with a coated end-effector blade while a comparable uncoated instrument was unable (in any reasonable length of time) to accomplish the same task; this due to the second listed cause. In use, various embodiments of the end-effector blades comprising one or more coatings as described herein, may improve tissue effects such as hemostasis by providing more uniform transection and/or coagulation of tissue.

As described herein, a coating may comprise one or more layers of materials formed on an outer surface of a body portion of an ultrasonic end-effector. The outer surface of the end-effector may be partially or completely coated with one or more than one layer of material. Each layer may comprise one or more materials. In other embodiments, one or more surface treatments may be applied either to the entire end-effector body or to a portion thereof. Still in other embodiments, the end-effector body may comprise a combination of coatings and applications of surface treatments. This combination may be applied to the entire end-effector or to a portion thereof.

In some embodiments, materials, surface treatments, and/or combinations thereof, may be suitably applied to an outer surface of the end-effector, or portion thereof, to produce an end-effector having a coefficient of friction that is lower than that of the end-effector base material alone. End-effectors with a lower coefficient of friction operate at lower temperatures and minimize generator lockout promoting faster cutting of tissue. In other embodiments, surface treatments may be suitably applied to an outer surface of the end-effector, or portion thereof, to produce an end-effector having a coefficient of friction that is greater than that of the end-effector base material alone. End effectors with a higher coefficient of friction improve the tissue sealing effects of the end-effector. Therefore, in some embodiments, it may be desirable to provide an end-effector with a lower coefficient of friction in the cutting region and a higher coefficient of friction in the tissue sealing region by applying various combinations of coatings and surface treatments to different portions of the end-effector.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and the scope of the various embodiments is defined solely by the claims. The features illustrated or described in connection with one embodiment may be combined with the features of other embodiments. Such modifications and variations are intended to be included within the scope of the appended claims.

It will be appreciated that the terms "proximal" and "distal" are used herein with reference to a clinician gripping a hand piece assembly of an ultrasonic surgical instrument. Thus, the end-effector is distal with respect to the more proximal hand piece assembly. It will be further appreciated that, for convenience and clarity, spatial terms such as "top" and "bottom" also are used herein with respect to the clinician gripping the hand piece assembly. However, surgical instruments are used in many orientations and positions, and these terms are not intended to be limiting and absolute.

FIG. 1 illustrates one embodiment of a multi-element end-effector 100. In the illustrated embodiment, the multi-element end-effector 100 comprises a clamp arm assembly 102, shown in an open position, operatively coupled to an ultrasonic surgical blade 112 (blade). The multiple-element end-effector 100 may be employed in a conventional clamping coagulating type ultrasonic instrument, for example. The clamp arm assembly 102 comprises a clamp arm 104 and a tissue pad 106 attached to the clamp arm 104. The blade 112 is an ultrasound-propagating element suitable for coupling to conventional ultrasonic surgical instruments. The blade 112 comprises a body 108 having a proximal end and a distal end and defining an elongated treatment region therebetween. The body 108 defines a longitudinal axis A extending between the proximal end and the distal end. The proximal end is adapted and configured to couple to an ultrasonic transducer either directly or through an ultrasonic transmission waveguide in a known manner. Mechanical vibrations produced by the ultrasonic transducer propagate along the transmission waveguide and are coupled to the proximal end of the body 108. The distal end of the body 108 is selected such that it is movable relative to the longitudinal axis A by the mechanical vibrations produced by the ultrasonic transducer. The distal end and the elongated treatment region is used to effect tissue (e.g., dissect, transect, cut, coagulate). These tissue effects may be enhanced by clamping the tissue between the camp arm 104 and the blade 112.

In one embodiment, a coating 116 may be formed or applied on at least a portion of an outer (e.g., external) surface of the body 108 that at least corresponds with the elongated treatment region. The coating 116 may comprise one or more than one layer 110 formed on the outer surface of the body 108. Each of the one or more than one layer 110 may consist of one or more than one material. Accordingly, in one embodiment, the layer 110 may in effect comprise several sub-layers. In one embodiment, the coating 116 may consist of a base layer (e.g., primer layer, first layer) as well as an overcoat layer (e.g., top layer, second layer) and one or more than one layer 110 therebetween. The surface area of the body 108 may include a surface treatment applied thereto to enhance the adhesion of the layer 110 of material to the body 108. The coated blade 112 enhances tissue effects during dissecting, transecting, cutting, and coagulating and improves the operational stability of the ultrasonic surgical instrument by minimizing or eliminating generator lockout.

Figure 2:
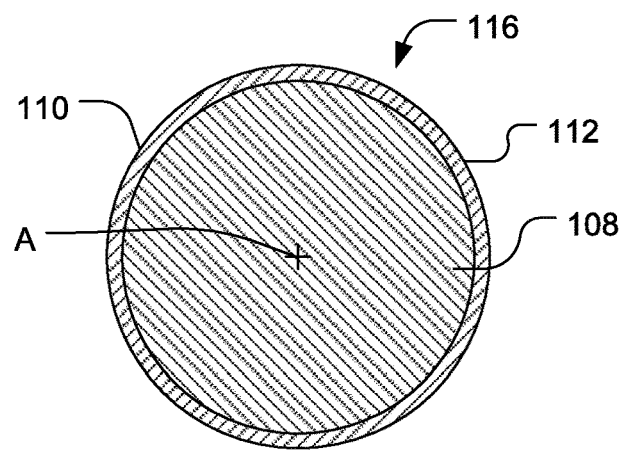
FIG. 2 illustrates a cross-sectional view of an ultrasonic blade portion of the multi-element end-effector shown in FIG. 1 taken along line 2-2.

FIG. 2 illustrates a cross-sectional view of the ultrasonic surgical blade 112 portion of the multi-element end-effector 100 taken along line 2-2 in FIG. 1. As shown in the cross-sectional view of FIG. 2 of the illustrated embodiment, the body 108 has a substantially circular cross sectional shape. In other embodiments, the body 108 may have any suitable cross sectional shape and may be symmetric or asymmetric in nature. For example, the body 108 may have a cross-sectional shape that defines a triangle, square, rectangle, pentagon, hexagon, any suitable polygon, or irregular shape, whether symmetric or asymmetric. The body 108 may be fabricated from a base material suitable for transmission of ultrasonic energy in the form of acoustic waves. The base material of the body 108 may comprise titanium (e.g., Ti6Al-4V ELI), aluminum, stainless steel, or any material or composition that is suitable for propagating acoustic waves efficiently, for example.

In one embodiment, the coating 116 may be formed as one layer 110 over at least a portion of the outer surface of the blade body 108. The layer 110 may consist of at least one material and in other embodiments may include multiple layers consisting of a base material (e.g., primer layer, first layer) and an overcoat material (e.g., top layer, second layer) as described in more detail herein with reference to FIGS. 3 and 4. The thickness of the layer 110 may be anywhere from about 0.0001 to about 0.010 inches (0.1 mils to 10 mils). The coating 116 may partially or completely cover the outer surface of the body 108. The layer 110 may be formed over the entire body 108 or may be formed over portions of the body 108. The coating 116 material may be selected to have a lower coefficient of friction than the body 108 material.

The layer 110 may comprise a variety of materials including polymeric and polymer containing materials. The term "polymeric materials" and the word polymer, as used herein, include, but are not limited to, homopolymers, copolymers, terpolymers, and the like. Non-limiting examples of polymeric and polymer-containing materials include tetrafluoroethylene (TFE) and hexafluoropropylene (HFP) copolymers (FEP), liquid FEP, FEP/ceramic composites, liquid FEP ceramic epoxy composites, polytetrafluoroethylene (PTFE or TEFLON®), and PTFE/ceramic composites. In other non-limiting embodiments, the layer 110 may comprise a dry film lubricant, such as, but not limited to, tungsten disulfide, molybdenum disulfide, graphite, and fluorinated polymers. Still in other non-limiting embodiments, the layer 110 may comprise ceramics, such as, but not limited to, metal oxides, metal nitrides, and metal carbides. Examples of ceramics, include, but are not limited to, chromium carbide, tungsten carbide, titanium nitride, alumina, and chromium nitride. Yet in other non-limiting embodiments, the layer 110 may comprise metals. Metals include, but are not limited to, aluminum, stainless steel, and molybdenum. In other non-limiting embodiments, the layer 110 may comprise a metallized ceramic, such as, but not limited to, stainless steel embedded in ceramic.

In various embodiments, the coating 116 may be formed in multiple layers including any of the materials previously discussed with respect to the layer 110. Examples of multi-layer coatings or composites include, but are not limited to, molybdenum/alumina/tungsten carbide, aluminum oxide/stainless steel, aluminum oxide/stainless steel 15/15%, chromium carbide/tungsten oxide, molybdenum/aluminum oxide/tungsten carbide, cobalt/molybdenum, graphite/tungsten oxide, aluminum oxide/stainless steel 25/30%, molybdenum/aluminum oxide/tungsten carbide/stainless steel, or chromium carbide/tungsten oxide, among other suitable materials.

In use, the blade 112 may be exposed to particularly harsh environments including ultrasonic vibrations, heat, and caustic solutions of blood and proteins referenced to herein as surgical matter. Consequently, the harsh operating environment tends to delaminate, erode, or wear the coating 116. Accordingly, the layer 110 should be applied to the body 108 using any suitable application technique that promotes good adhesion between the base material of the body 108 and the layer 110 to prevent or minimize delamination, erosion, or wear of the layer 110 from the body 108. The layer 110 may be applied to the body using suitable material application techniques: coating, dipping, spraying, brushing, drying, melting, laser curing, anodizing, electroplating, electroless chemical deposition, sintering, fused curing, physical vapor deposition (PVC), chemical vapor deposition (CVD), thermal spray, thick film high velocity oxygen fuel (HVOF) plasma, and any other suitable material application techniques. Other well known material deposition techniques are described in U.S. Pat. Nos. 7,041,088 and 6,663,941, which are incorporated herein by reference. One suitable material application technique is a process developed by Integrated Surgical Sciences, Corp. (ISSC) of Sedalia, Colo., USA. Alternatively, the materials for forming the coating 116, or any constituent material forming the various layers thereof, may be purchased from ISSC and applied in accordance with any suitable material application techniques.

In various embodiments, a surface treatment or a plurality of surface treatments may be applied to the body 108 using a variety of techniques: peening, sand blasting, micro blasting, bead blasting, knurling, engraving, chemical treatment such as acid or base etching, laser etching, plasma etching, corona discharge etching, heat etching, carving, scoring, vibratory deburring, abrasive flow machining, and other techniques. The surface treatment can advantageously improve the adhesion of the layer 110 to the surface of the body 108. However, care should be taken when applying surface treatments to prevent damage to the body 108 during application, which later may lead to failure of the blade 112 during use. For example, surface bead blasting may increase the stress concentrations in the end-effector body 108 and may lead to the failure of the end-effector during use. FIG. 4A illustrates one example of a surface treatment 108A that may be applied to the surface of the body 108 to enhance the adhesion of the layer 110 to the surface of the body 108.

In use, the blade 112 comprising the coating 116 formed over the body 108 provides several advantages such as improved cutting and coagulating functions over an uncoated blade. In one embodiment, the coating 116 has a coefficient of friction that is lower than the coefficient of friction of the surface of the base material of the body 108 alone. Thus, the coating 116 forms a lubricious layer over at least a portion of the body 108. The blade 112 comprising the lubricious coating 116 provides several benefits and/or advantages over conventional uncoated bare end-effector blades. For example, the coated blade 112 provides improved tissue cutting (e.g., transecting) along the longitudinal length of the blade 112 resulting in more uniform transection of tissue, improved vessel sealing and homogeneity of the tissue layer, and improved thermal and structural properties of the blade 112, which facilitates more uniform transection of the tissue. The coated blade 112 may further facilitate uniform serosa-to-serosa adhesion along the cut length of the tissue, thus minimizing or eliminating discontinuities of adhesion along the tissue cut length, which commonly occur with conventional uncoated blades. The lubricious property of the coating 116 also minimizes the adhesion of surgical matter to the surface of the blade 112 during surgical procedures. As previously discussed, "surgical matter" includes coagulants, proteins, blood, tissue, and/or other constituent fluids, which may be present during a surgical procedure and tend to desiccate and adhere to the surface of uncoated blades raising the interface impedance of the blade. As previously discussed, to compensate for the increased impedance, the ultrasonic generator supplies increasing amounts of power to the blade to continue transecting tissue until the power delivered by the generator exceeds a predetermined threshold at which time the generator shuts down or goes into "lockout." As previously discussed, lockout is a condition where the impedance of the end-effector is so high that the generator is unable to provide meaningful amounts of the power to the tissue. Therefore, by minimizing the deposition, buildup, or adhesion of surgical matter, the coated blade 112 reduces the electrical power required to operate the blade 112 when transecting tissue. As a result, the coated blade 112 minimizes the power supplied by the generator and minimizes or prevents lockouts of the generator.

Those skilled in the art will appreciate that ultrasonic end-effector blades are relatively efficient and that the electrical power required for driving the end-effector blade correlates well with the power delivered to tissue loads. Essentially, the lubricious coating 116 reduces the friction between the blade 112 and the tissue, thus reducing the thermal profile of the blade 112. Because the tissue does not adhere to the coating 116, it releases from the blade 112 more easily and uniformly than an uncoated blade requiring less average power draw (less total energy applied) and less time (even less total energy applied) than an uncoated blade giving a truly unexpected and synergistic effect. In certain instances, the time required to transect tissue, for example, may be reduced by as much as 34%. Additionally, because the coated blade 112 reduces or minimizes the number of generator lockouts that may occur over a surgical procedure, the coated blade 112 even more substantially reduces the overall time required to complete the surgical procedure.

It is generally well known that tissue pads tend to degrade and wear over time due to frictional engagement with a blade when no tissue is present therebetween. The lubricious coating 116, however, also lowers the coefficient of friction between the coated blade 112 and the tissue pad 106 and as a result can extend the life of the tissue pad 106. Accordingly, the coated blade 112 can reduce or minimize the degradation and deterioration of the tissue pad 106 caused by abrasion and frictional engagement with the blade 112. Consequently, the coated blade 112 can substantially extend the operational life of the tissue pad 106 when compared to conventional uncoated blades.

FIG. 3 illustrates one embodiment of a multi-element end-effector 200. In the illustrated embodiment, the multi-element end-effector 200 comprises a clamp arm assembly 202, shown in an open position, operatively coupled to an ultrasonic surgical blade 212 (blade). The multiple-element end-effector 200 may be employed in clamping coagulating type ultrasonic instruments, for example. The clamp arm assembly 202 comprises a clamp arm 104 and a tissue pad 106 attached thereto. The blade 212 is an ultrasound-propagating element suitable for use in ultrasonic surgical instruments. The body 108, previously discussed with reference to FIGS. 1 and 2, forms a portion of the blade 212. As previously discussed, the body 108 comprises a proximal end and a distal end and defines an elongated treatment region therebetween. The proximal end is adapted and configured to couple to an ultrasonic transducer either directly or through an ultrasonic transmission waveguide. The distal end and the treatment region is used to effect tissue (e.g., dissect, transect, cut, coagulate). In one embodiment, a coating 216 is formed on at least a portion of the outer surface of the body 108 that at least corresponds with the elongated treatment region. The coating 216 may comprise at least two layers 210, 214 of materials. In the illustrated embodiment, a primer layer 214 (e.g., base layer, first layer) may be formed on the outer surface of the body 108. An overcoat layer 210 (e.g., top layer, second layer) may be formed over the primer layer 214. In one embodiment, the overcoat layer 210 may be formed over a portion of the primer layer 214. The primer layer 214 forms a suitable adhesive bond with the outer surface of the body 108 and is formulated to enhance the adhesion of the overcoat layer 210 to the body 108. The primer layer 214 and/or the overcoat layer 210 each may comprise multiple layers of materials. The layers 210, 214 may be formed on the body 108 using any suitable material application technique including techniques discussed herein with respect to FIGS. 1 and 2 (e.g., the coating application process developed by ISSC).

FIG. 4 illustrates a cross-sectional view of the ultrasonic surgical blade 212 portion of the multi-element end-effector 200 taken along line 4-4 in FIG. 3. As shown in the cross-sectional view of FIG. 4, in the illustrated embodiment, the coating 216 comprises multiple layers 214, 210 of materials. The primer layer 214 is the first layer applied to the body 108. In various embodiments, the primer layer 214 may comprise a polymer or polymeric materials and/or ceramic. In various embodiments, the primer layer 214 may comprise FEP or liquid FEP. In one embodiment, the primer layer 214 may comprise aluminum oxide or any suitable material composition containing aluminum oxide. In another embodiment the primer layer 214 may comprise titanium nitride or any suitable material composition containing titanium nitride. The overcoat layer 210 is then applied over the primer layer 214 material to form the top layer of the coating 216, which has lubricious properties similar to the coating 116 previously discussed with reference to FIGS. 1 and 2. The overcoat layer 210 may be applied to a portion of the primer layer 214 or may be applied over the entire primer layer 214. The overcoat layer 210 may comprise a variety of materials including polymeric and polymer containing materials. As previously discussed, the term "polymeric materials" and the word polymer, as used herein, include, but are not limited to, homopolymers, copolymers, terpolymers, and the like. As previously discussed, non-limiting examples of polymeric and polymer-containing materials include FEP, liquid FEP, FEP/ceramic composites, liquid FEP ceramic epoxy composites, PTFE, and PTFE/ceramic composites. In other non-limiting embodiments, the overcoat layer 210 may comprise a dry film lubricant, such as, but not limited to, tungsten disulfide, molybdenum disulfide, graphite, and fluorinated polymers. Still in other non-limiting embodiments, the overcoat layer 210 may comprise ceramics, such as, but not limited to, metal oxides, metal nitrides, and metal carbides. Examples of ceramics, include, but are not limited to, chromium carbide, tungsten carbide, titanium nitride, alumina, and chromium nitride. Yet in other non-limiting embodiments, the overcoat layer 210 may comprise metals. Metals include, but are not limited to, aluminum, stainless steel, and molybdenum. In other non-limiting embodiments, the overcoat layer 210 may comprise a metallized ceramic, such as, but not limited to, stainless steel embedded in ceramic. In one embodiment, the overcoat layer 210 may be applied using conventional powder coating techniques.

FIG. 4A is an enlarged view of the cross-sectional portion of one embodiment of the blade 216 shown in FIG. 4. As shown in FIG. 4A, in one embodiment, the surface of the body 108 may be prepared with a suitable surface treatment 108A prior to the application of the primer layer 214 to further enhance or promote the adhesion of the primer layer 214 material to the outer surface of the body 108. In another embodiment, a surface treatment may be applied to the surface of the primer layer 214 prior to the application of the overcoat layer 210 to enhance the adhesion of the overcoat layer 210 to the primer layer 214. The surface treatment 108A may be applied the surface of the body 108 using any of the techniques previously described with reference to FIGS. 1 and 2 (e.g., peening, micro blasting, sand blasting, bead blasting, knurling, engraving, chemical treatment such as acid or base etching, laser etching, plasma etching, corona discharge etching, heat etching, carving, scoring, and other techniques) to produce a predetermined surface roughness $R_A$ of about 16 microinches (µin) to about 256 µin. In one embodiment, a surface treatment may be applied to an outer surface of the body 108 to produce a predetermined surface roughness $R_A$ of about 16 µin to about 63 µin, for example. However, other surface roughnesses also may be produced. After coating the body 108 with the primer layer 214, the preferred surface roughness $R_A$ range of the finished product is about 16 µin to about 32 µin.

Figure 4B:
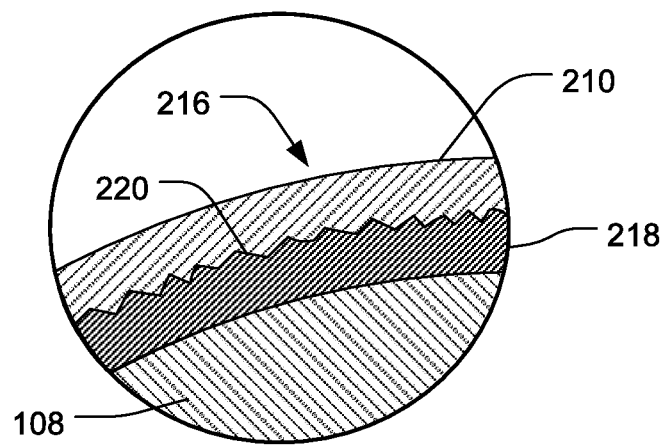
FIG. 4B is an enlarged view of a portion of the cross-sectional portion of one embodiment of the ultrasonic blade portion of the multi-element end-effector shown in FIG. 3.

FIG. 4B is an enlarged view of the cross-sectional portion of one embodiment of the blade 216 shown in FIG. 4. As shown in FIG. 4B, in one embodiment, a primer layer 218 may be formed directly on the outer surface of the body 108. In one embodiment, the primer layer 218 has a surface 220 having a predetermined surface roughness that enhances or promotes adhesion of the topcoat layer 210 to the primer layer 218. In one embodiment, the surface 220 may be achieved using a rough titanium nitride coating as the primer layer 218. The rough surface 220 of the primer layer 218 provides a good bonding surface for a topcoat layer 210 having a low coefficient of friction. The primer layer 218 comprising titanium nitride provides a good bond to the outer surface of the body 108 without the need for a surface treatment. In another embodiment, the surface 220 may be achieved using a rough aluminum oxide coating as the primer layer 218 to provide a good bonding surface for a topcoat layer 210 having a low coefficient of friction. The aluminum oxide coating also may provide a good bond to the outer surface of the body 108 without the need for a surface treatment.

Figure 4C:
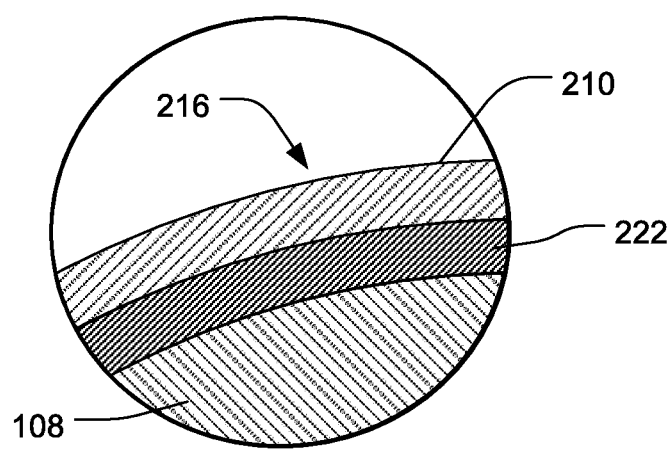
FIG. 4C is an enlarged view of a portion of the cross-sectional portion of one embodiment of the ultrasonic blade portion of the multi-element end-effector shown in FIG. 3.

FIG. 4C is an enlarged view of the cross-sectional portion of one embodiment of the blade 216 shown in FIG. 4. As shown in FIG. 4C, in one embodiment, a primer layer 222 may be formed directly on the outer surface of the body 108. In one embodiment, the primer layer 222 has a surface that enhances or promotes adhesion of the topcoat layer 210 to the primer layer 222.

In various embodiments, any of the primer layers 214, 218, 222 may comprise aluminum oxide, titanium nitride, FEP, or liquid FEP, which passivates the surface of the body 108 for better adhesion of the overcoat layer 210. In various embodiments, any of the primer layers 214, 218, 222 may consist essentially of aluminum oxide, titanium nitride, FEP or liquid FEP. In other embodiments, any of the primer layers 214, 218, 222 may comprise any of the base materials previously discussed with reference to FIGS. 2-4.

Figure 5:
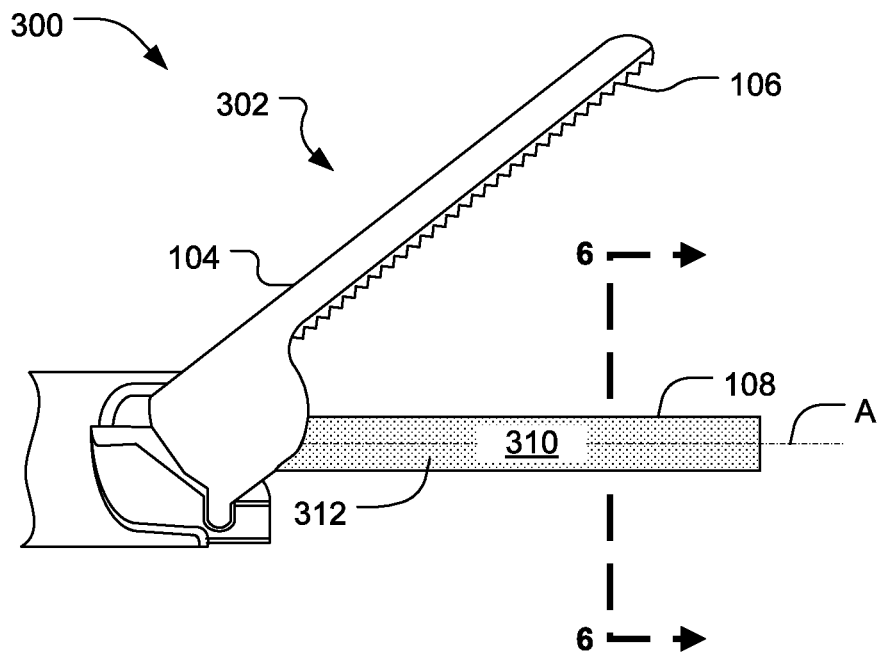
FIG. 5 illustrates one embodiment of a multi-element end-effector.

FIG. 5 illustrates one embodiment of a multi-element end-effector 300. In the illustrated embodiment, the multi-element end-effector 300 comprises a clamp arm assembly 302, shown in an open position, operatively coupled to an ultrasonic surgical blade 312 (blade). The multiple-element end-effector 300 may be employed in clamping coagulating type ultrasonic instruments, for example. The clamp arm assembly 302 comprises a clamp arm 104 and a tissue pad 106 attached thereto. The blade 312 is an ultrasound-propagating element suitable for use in ultrasonic surgical instruments. The body 108, previously discussed with reference to FIGS. 1-4, forms a portion of the blade 312. As previously discussed, the body 108 comprises a proximal end and a distal end and defines an elongated treatment region therebetween. The proximal end is adapted and configured to couple to an ultrasonic transducer either directly or through an ultrasonic transmission waveguide. The distal end and the elongated treatment region is used to effect tissue (e.g., dissect, transect, cut, coagulate). A surface treatment 310 may be applied to an outer surface of the body 108 that at least corresponds with the elongated treatment region. Those skilled in the art will appreciate, that the surface treatment 310 having a particular surface roughness $R_A$ may be produced using the well known techniques previously described with reference to FIG. 2, for example, provided that the underlying structure of the body 108 is not compromised.

Figure 6:
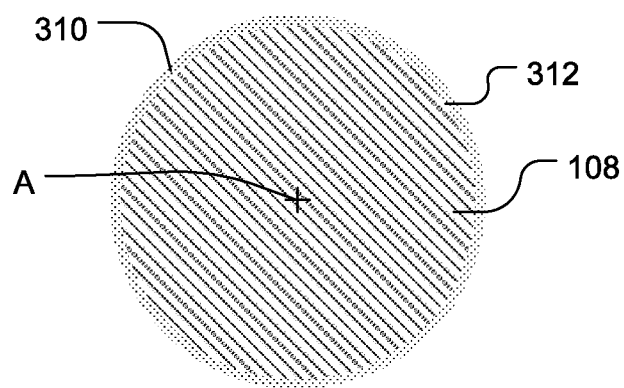
FIG. 6 illustrates a cross-sectional view of the ultrasonic blade portion of the multi-element end-effector shown in FIG. 5 taken along line 6-6.

FIG. 6 illustrates a cross-sectional view of the ultrasonic blade 312 portion of the multi-element end-effector 300 taken along line 6-6 in FIG. 5. With reference to FIGS. 5 and 6, in one embodiment, the surface treatment 310 (e.g., roughness) may be formed or applied to the outer surface of the body 108 or may be formed on the outer surface of a coating layer applied to the body 108 as described later herein with reference to FIGS. 7 and 8. A suitable surface treatment 310 has a coefficient of friction that is greater than the coefficient of friction of the untreated outer surface area of the body 108. A rough "frictional" surface treatment 310 has a predetermined surface roughness $R_A$ of about 16 µin to about 256 µin. In one embodiment, the rough "frictional" surface treatment 310 has a predetermined surface roughness $R_A$ of about 32 µin. The surface treatment 310 may be formed on the outer surface of the body 108 to assist the blade 312 to frictionally engage (grip) and stabilize the walls of blood vessels and as a result provide improved and more reliable vessel sealing. Because of the rougher surface treatment 310, the blade 312 remains engaged with the tissue long enough to prevent the vessel walls from pulling away from the seal line. Consequently, this promotes the communication of tissue collagen from one side of the seal line to the other to create a very reliable seal, as will be appreciated by those skilled in the art.

Figure 7:
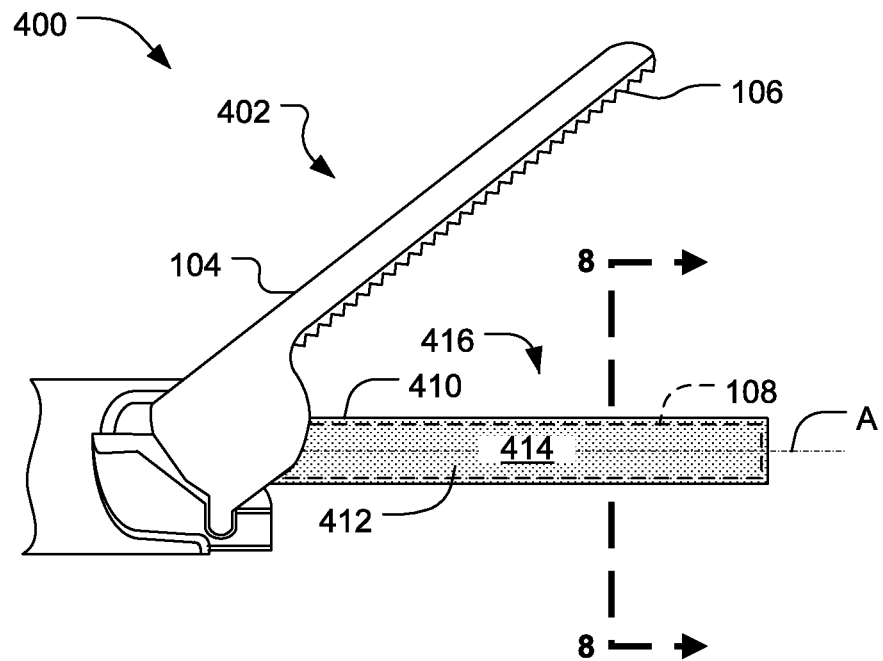
FIG. 7 illustrates one embodiment of a multi-element end-effector.

FIG. 7 illustrates one embodiment of a multi-element end-effector 400. In the illustrated embodiment, the multi-element end-effector 400 comprises a clamp arm assembly 402, shown in an open position, operatively coupled to an ultrasonic surgical blade 412 (blade). The multiple-element end-effector 400 may be employed in a clamping coagulating ultrasonic instrument, for example. The clamp arm assembly 402 comprises a clamp arm 104 and a tissue pad 106 attached thereto. The blade 412 is an ultrasound-propagating element suitable for use in ultrasonic surgical instruments. The body 108, as previously discussed with reference to FIGS. 1-6, forms a portion of the blade 412. As previously discussed, the body 108 comprises a proximal end and a distal end and defines an elongated treatment region therebetween. The proximal end is adapted and configured to couple to an ultrasonic transducer either directly or through an ultrasonic transmission waveguide. The distal end and the treatment region are used to effect tissue (e.g., dissect, transect, cut, coagulate). In one embodiment, a coating 416 comprising a first layer 410 of material may be formed on an outer surface of the body 108 using any of the material application techniques previously described (e.g., the coating application process developed by ISSC). The first layer 410 may comprise any of the polymeric materials, dry film lubricants, ceramics, metals, and metallized ceramics previously described with reference to FIG. 2.

Figure 8:
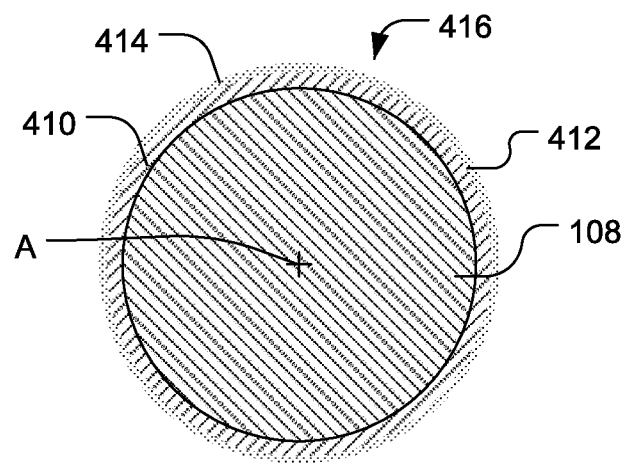
FIG. 8 illustrates a cross-sectional view of the ultrasonic blade portion of the multi-element end-effector shown in FIG. 7 taken along line 8-8.

FIG. 8 illustrates a cross-sectional view of the ultrasonic blade 412 portion of the multi-element end-effector 400 taken along line 8-8 in FIG. 7. A surface treatment 414 having a predetermined roughness $R_A$ of about 16 μin to about 256 μin may be produced over the layer 410 using any of the techniques previously discussed with reference to FIG. 2. The body 108 defines a longitudinal axis A extending between the proximal end and the distal end. The distal end of the body 108 is movable relative to the longitudinal axis A by the vibrations produced by the transducer propagating along the longitudinal axis A. With reference to FIGS. 7 and 8, in one embodiment, the surface treatment 414 having a predetermined surface roughness $R_A$ of about 16 μin to about 256 μin may be formed over the first layer 410, or portions thereof. However, other suitable values surface roughness $R_A$ may be successfully produced. For example, a surface treatment of a predetermined surface roughness $R_A$ having a coefficient of friction that is greater than the coefficient of friction of the first layer 410 may be produced over the first layer 410 to assist the blade 412 in gripping and stabilizing the walls of blood vessels and producing better, more reliable, vessel seals. The surface treatment 414, having a coefficient of friction slightly greater than the first layer 410, enables the blade 412 to remain engaged with the tissue long enough to prevent the joined vessels walls from pulling away or shrinking away from the seal line prior to completing the sealing operation. It will be appreciated, that the surface treatment 414 may be formed over a portion of the body 108 in order to take advantage of the lubricious properties of the coating 410 for cutting operations while also taking advantage of the rougher surface treatment 414 portion for sealing operations.

Figure 9:
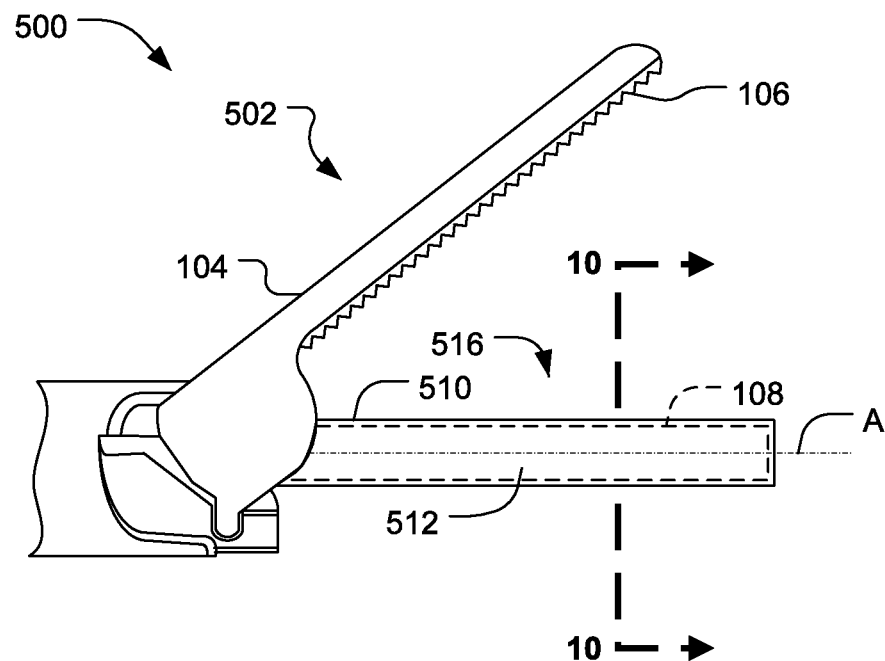
FIG. 9 illustrates one embodiment of a multi-element end-effector.

FIG. 9 illustrates one embodiment of a multi-element end-effector 500. In the illustrated embodiment, the multi-element end-effector 500 comprises a clamp arm assembly 502, shown in an open position, operatively coupled to an ultrasonic surgical blade 512 (blade). The multiple-element end-effector 500 may be employed in clamping coagulating type ultrasonic instruments, for example. The clamp arm assembly 502 comprises a clamp arm 104 and a tissue pad 106 attached thereto. The blade 512 is an ultrasound-propagating element suitable for use in ultrasonic surgical instruments. The body 108, as previously discussed with reference to FIGS. 1-8 forms a portion of the blade 512. As previously discussed, the body 108 comprises a proximal end and a distal end and defines an elongated treatment region therebetween. The proximal end is adapted and configured to couple to an ultrasonic transducer either directly or through an ultrasonic transmission waveguide. The distal end and the treatment region are used to effect tissue (e.g., dissect, transect, cut, coagulate).

Figure 10:
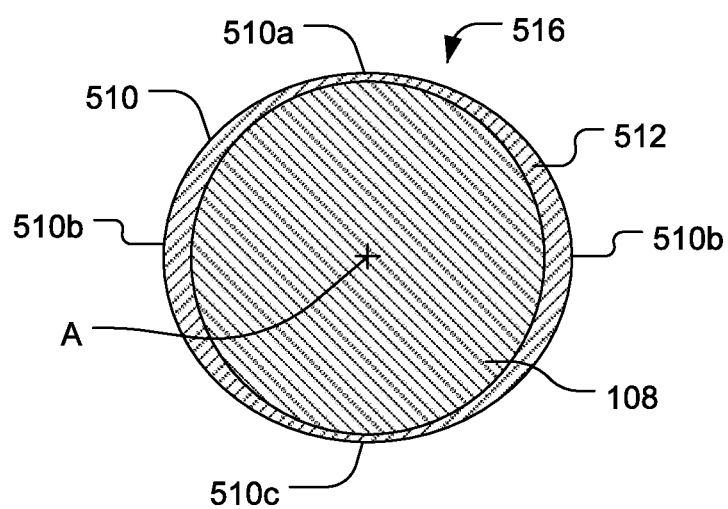
FIG. 10 illustrates a cross-sectional view of the ultrasonic blade portion of the multi-element end-effector shown in FIG. 9 taken along line 10-10.

FIG. 10 illustrates a cross-sectional view of the ultrasonic blade 512 portion of the multi-element end-effector 500 taken along line 10-10 in FIG. 9. A coating 516 comprising a layer 510 of material may be formed on at least a portion of an outer surface of the blade body 108. One or more than one layer 510 of material may be formed on the body 108 using any suitable application technique discussed herein (e.g., the coating application process developed by ISSC).

With reference to FIGS. 9 and 10, in one embodiment, the one or more than one layer 510 of material may be formed on the blade 512 non-uniformly such that the layer 510 has variable thickness about the outer surface of the body 108. In the illustrated embodiment, the layer 510 is formed thicker to assist thermal bonding. In one embodiment, a thinner layer 510a may be formed on a top surface portion of the body 108 where the blade 516 comes in contact with the tissue pad 106 and thicker layers 510b of the material may be formed on lateral surface portions of the body 108.

A layer 510c of any suitable thickness may be formed on the bottom surface portion of the body 108 opposite of the top surface portion. In the illustrated embodiment, the layer 510c on the bottom surface portion of the body 108 is formed with the same thickness as the thinner layer 510a. In other embodiments, the layer 510c at the bottom surface portion of the body 108 may be formed with the same thickness as the thicker layers 510b, thicker than the layers 510b, or other suitable thicknesses. In other embodiments, multiple layers may be formed of varying thicknesses on the lateral portions of the body 108 to prevent excessive thermal damage to these areas of the seal. The one or more than one layer 510 of material may comprise any of the polymeric materials, dry film lubricants, ceramics, metals, and metal-lized ceramics previously discussed with reference to FIG. 2. In other embodiments, a primer layer and/or a surface treatment may be applied to the outer surface of the body 108 prior to the application of the one or more than one layer 510 of material. To the extent that one embodiment of the blade 512 comprises a primer layer, the primer layer may comprise any of the base materials previously discussed with reference to FIGS. 2 and 4. To the extent that one embodiment of the blade 512 comprises a surface treatment, the surface treatment may be applied in accordance with the techniques previously discussed with reference to FIGS. 2 and 4A.

Figure 11:
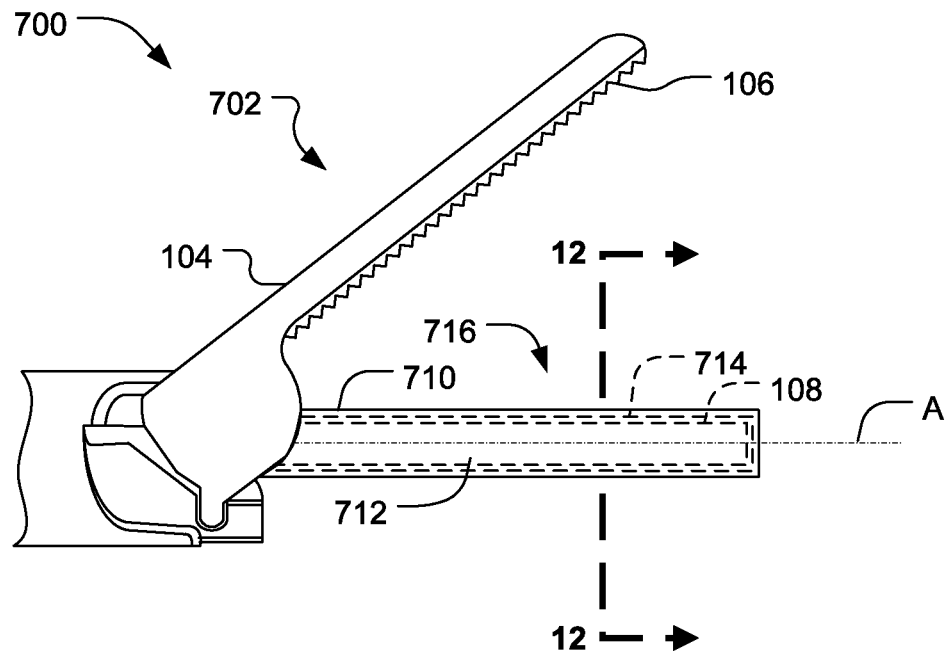
FIG. 11 illustrates one embodiment of a multi-element end-effector.

FIG. 11 illustrates one embodiment of a multi-element end-effector 700. In the illustrated embodiment, the multi-element end-effector 700 comprises a clamp arm assembly 702, shown in an open position, operatively coupled to an ultrasonic surgical blade 712 (blade). The multiple-element end-effector 700 may be employed in clamping coagulating type ultrasonic instruments, for example. The clamp arm assembly 702 comprises a clamp arm 104 and a tissue pad 106 attached thereto. The blade 712 is an ultrasound-propagating element suitable for use in ultrasonic surgical instruments. The body 108, as previously discussed with reference to FIGS. 1-10, forms a portion of the blade 712. As previously discussed, the body 108 comprises a proximal end and a distal end defining an elongated treatment region. The proximal end is adapted and configured to couple to an ultrasonic transducer either directly or through an ultrasonic transmission waveguide. The distal end and the treatment region are used to effect tissue (e.g., dissect, transect, cut, coagulate).

Figure 12:
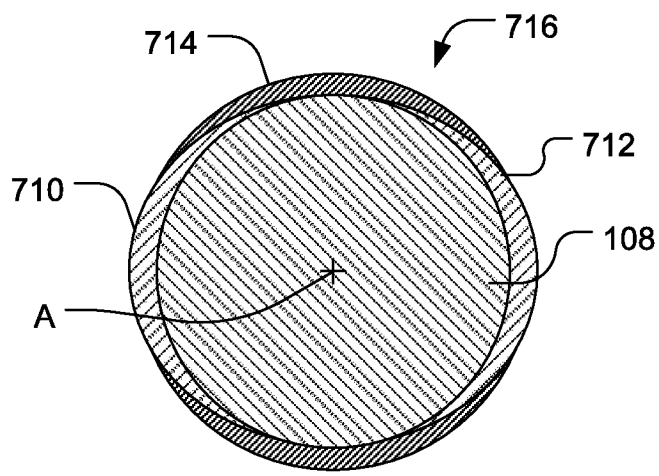
FIG. 12 illustrates a cross-sectional view of the ultrasonic blade portion of the multi-element end-effector shown in FIG. 11 taken along line 12-12.

FIG. 12 illustrates a cross-sectional view of the ultrasonic blade 712 portion of the multi-element end-effector 700 taken along line 12-12 in FIG. 11. In various embodiments, a coating 716 may be formed on the outer surface of the blade body 108. The coating 716 may comprise one or more layers of materials, surface treatments, and/or combinations thereof. In the illustrated embodiment, a first layer 710 and a second layer 714 are formed on the outer surface of the body 108. In one embodiment, the second layer 714 may be formed over a portion of the first layer 710. The one or more material layers 710, 714 may be formed on the body 108 using any suitable material application technique including techniques discussed herein (e.g., the coating application process developed by ISSC). As shown in FIG. 12, the blade 712 may comprise multiple layers of materials, each of varying thicknesses. The first layer 710 may be formed thicker on the lateral surface portions of the body 108 and may be formed thinner on the top surface portions of the body 108, for example, where the blade 712 contacts the tissue pad 106. A second layer 714 may be formed on the first layer 710. The second layer 714 may be formed thicker on the top surface portion of the body 108 where the blade 712 contacts the tissue pad 106 is relatively thinner on the lateral surface portions of the body 108. In one material application technique, the first layer 710 is applied to the body 108 and the second layer 714 is subsequently applied over on the first layer 710 or, as shown in FIG. 12, over portions of the first layer 710. The first and second layers 710, 714 may comprise any of the polymeric materials, dry film lubricants, ceramics, metals, and metallized ceramics previously discussed with reference to FIGS. 2 and 4. In other embodiments, a primer layer and/or a surface treatment may be applied to the outer surface of the body 108 prior to the application of the first and second layers 710, 714. To the extent that one embodiment of the blade 712 comprises a primer layer, the primer layer may comprise any of the base materials discussed with reference to FIGS. 2 and 4. To the extent that one embodiment of the blade 712 comprises a surface treatment, the surface treatment may be applied in accordance with the techniques previously discussed with reference to FIGS. 2 and 4A.

Figure 13:
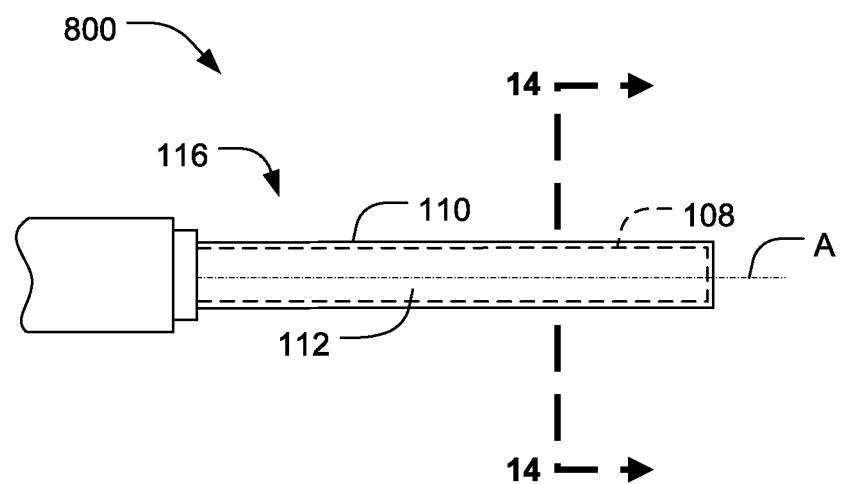
FIG. 13 illustrates one embodiment of a single element end-effector.

FIG. 13 illustrates one embodiment of a single element end-effector 800. In one embodiment, the single element end-effector 800 comprises the ultrasonic surgical blade 112 (blade), shown and described with reference to FIGS. 1 and 2. The single-element end-effector 800 may be a scalpel, hook, or ball coagulator, for example. As previously discussed, the coating 116 may be formed on at least a portion of an outer surface of the body 108. The coating 116 also may comprise one or more layers 110 formed on the outer surface of the body 108.

Figure 14:
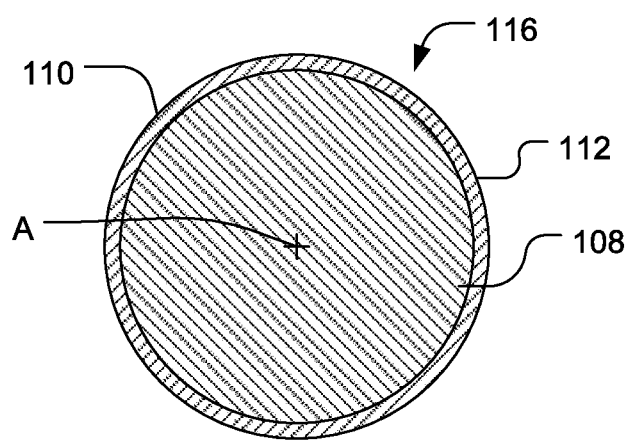
FIG. 14 illustrates a cross-sectional view of an ultrasonic blade portion of the single element end-effector shown in FIG. 13 taken along line 14-14.

FIG. 14 illustrates a cross-sectional view of the ultrasonic blade 112 portion of the single element end-effector 800 taken along line 14-14 in FIG. 13. As shown in the cross-sectional view of FIG. 14, in the illustrated embodiment, the blade 112 and the body 108 may have a substantially circular cross sectional shape. In other embodiments, the shape of the blade 112 may be selected according to the type of end-effector used, such as any of the shapes described with reference to FIG. 2.

Figure 15:
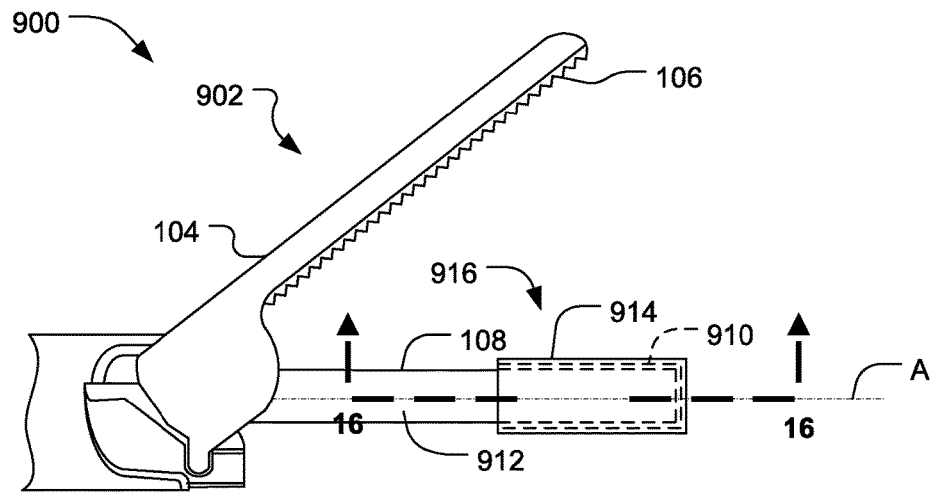
FIG. 15 illustrates one embodiment of a multi-element end-effector.

FIG. 15 illustrates one embodiment of a multi-element end-effector 900. In the illustrated embodiment, the multi-element end-effector 900 comprises a clamp arm assembly 902, shown in an open position, operatively coupled to an ultrasonic surgical blade 912 (blade). The multiple-element end-effector 900 may be employed in clamping coagulating type ultrasonic instruments, for example. The clamp arm assembly 902 comprises a clamp arm 104 and a tissue pad 106 attached thereto. The blade 912 is an ultrasound-propagating element suitable for use in ultrasonic surgical instruments. The body 108, as previously discussed with reference to FIGS. 1-14, forms a portion of the blade 912. As previously discussed, the body 108 comprises a proximal end and a distal end defining an elongated treatment region. The proximal end is adapted and configured to couple to an ultrasonic transducer either directly or through an ultrasonic transmission waveguide. The distal end and the treatment region are used to effect tissue (e.g., dissect, transect, cut, coagulate). A coating 916 may be formed on at least a portion of an outer surface of the body 108. The coating 916 also may comprise one or more layers 910, 914 formed on the outer surface of the body 108.

Figure 16:
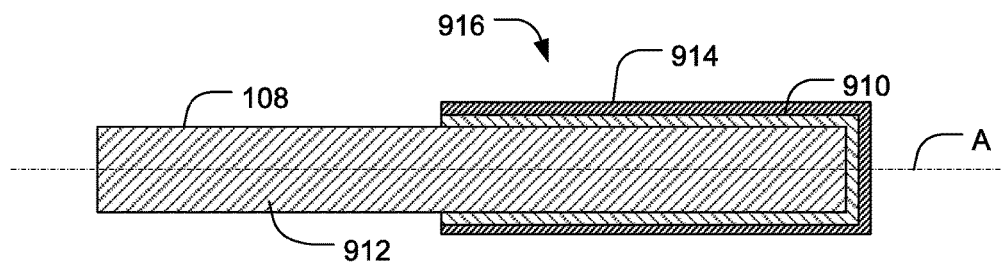
FIG. 16 illustrates a cross-sectional view of an ultrasonic blade portion of the multi-element end-effector shown in FIG. 15 taken along line 16-16.

FIG. 16 illustrates a cross-sectional view of the ultrasonic blade 912 portion of the multi-element end-effector 900 taken along line 16-16 in FIG. 15. In various embodiments, the coating 916 may be formed on a portion of the outer surface of the blade body 108. In one embodiment, the coating 916 may comprise a first layer 910 (e.g., primer layer, first layer) and a second layer 914 (e.g., topcoat layer, second layer). In one embodiment, the second layer 914 may be formed over a portion of the first layer 910. The first and second layers 910, 914 may comprise any of the polymeric materials, dry film lubricants, ceramics, metals, and metallized ceramics previously discussed with reference to FIGS. 2 and 4. In other embodiments, a surface treatment may be applied to the outer surface of the body 108 prior to the application of the first and second layers 910, 914. To the extent that one embodiment of the blade 912 comprises a surface treatment, the surface treatment may be applied in accordance with the techniques previously discussed with reference to FIGS. 2 and 4A.

Figure 17:
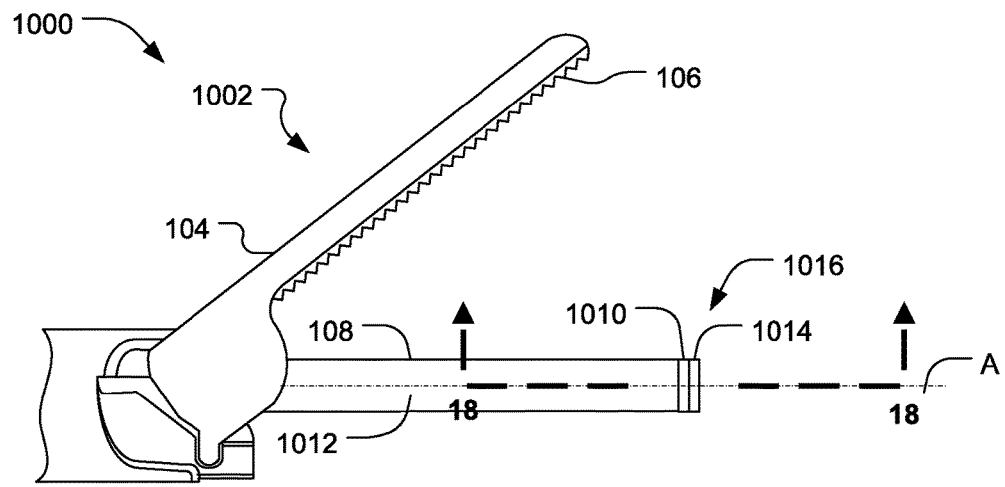
FIG. 17 illustrates one embodiment of a multi-element end-effector.

FIG. 17 illustrates one embodiment of a multi-element end-effector 1000. In the illustrated embodiment, the multi-element end-effector 1000 comprises a clamp arm assembly 1002, shown in an open position, operatively coupled to an ultrasonic surgical blade 1012 (blade). The multiple-element end-effector 1000 may be employed in clamping coagulating type ultrasonic instruments, for example. The clamp arm assembly 1002 comprises a clamp arm 104 and a tissue pad 106 attached thereto. The blade 1012 is an ultrasound-propagating element suitable for use in ultrasonic surgical instruments. The body 108, as previously discussed with reference to FIGS. 1-16, forms a portion of the blade 1012. As previously discussed, the body 108 comprises a proximal end and a distal end defining an elongated treatment region. The proximal end is adapted and configured to couple to an ultrasonic transducer either directly or through an ultrasonic transmission waveguide. The distal end and the treatment region are used to effect tissue (e.g., dissect, transect, cut, coagulate). A coating 1016 may be formed on at least a portion of an outer surface of the body 108. The coating 1016 also may comprise one or more layers 1010, 1014 formed on the outer surface of the body 108.

Figure 18:
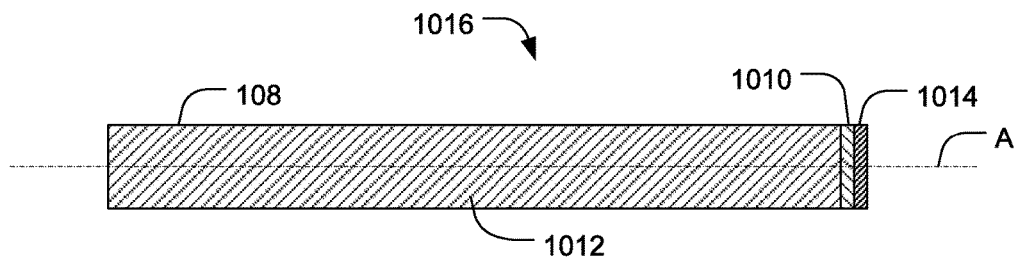
FIG. 18 illustrates a cross-sectional view of an ultrasonic blade portion of the multi-element end-effector shown in FIG. 17 taken along line 18-18.

FIG. 18 illustrates a cross-sectional view of the ultrasonic blade 1012 portion of the multi-element end-effector 1000 taken along line 18-18 in FIG. 17. In various embodiments, a coating 1016 may be formed on a distal end of the outer surface of the blade body 108. The coating 1016 may comprise a first layer 1010 (e.g., a primer layer, first layer) and a second layer 1014 (e.g., a topcoat layer, second layer) of material, surface treatment, and/or combination thereof. The first and second layers 1010, 1014 may comprise any of the polymeric materials, dry film lubricants, ceramics, metals, and metallized ceramics previously discussed with reference to FIGS. 2 and 4. In other embodiments, a surface treatment may be applied to the outer surface of the body 108 prior to the application of the first and second layers 1010, 1014. To the extent that one embodiment of the blade 1012 comprises a surface treatment, the surface treatment may be applied in accordance with the techniques previously discussed with reference to FIGS. 2 and 4A.

With reference now to FIGS. 1-18, in various embodiments, the blade 112 (212, 312, 412, 512, 612, 712, 912, 1012) in addition to the shown circular cross sectional shape may have various cross sectional forms or shapes, which may be symmetrical or asymmetrical in nature. For example, the blade may comprise a square, rectangular, triangular, or other polygonal cross-sectional shapes. As previously discussed, in various embodiments, the body 108 also may comprise a variety of symmetrical or asymmetrical shapes. For example, the body 108 may be curved in one or more directions. More details regarding curved or asymmetric blades are described in U.S. Pat. No. 6,283,981, which is incorporated herein by reference.

In still other embodiments, the body 108 may be configured with a neck or transition portion that protrudes from the proximal end of the treatment region. The neck portion may be configured to attach to an ultrasonic transmission waveguide by a stud, weld, glue, quick connect, or other suitable attachment methods, for example. In various other embodiments, the body 108 and the ultrasonic transmission waveguide may be formed as a single unitary body. In either configuration, the ultrasonic transmission waveguide may have gain steps to amplify the mechanical vibrations transmitted to the body 108 as is well known in the art.

With reference to FIGS. 1-18, in one embodiment, any of the end-effectors described herein (e.g., blades 112, 212, 312, 412, 512, 612, 712, 912, 1012) may comprise coatings formed of soft or deflectable layers of material to establish frictional engagement (e.g., gripping) with the tissue for improved tissue sealing. Examples of deflectable materials include materials having a durometer hardness of Shore D from about 25 to about 70 Shore units. In other embodiments, the end-effector may include coatings formed of layers of material combined with other technologies such as augmentation via clips and other fasteners. In other embodiments, the end-effector may include a lumen formed through the longitudinal axis A to facilitate suction and removal of expressed fluids from the sealing site to prevent excessive thermal damage to a non-value-added portion of the seal. In other embodiments, the end-effector may include a coating formed of one or more layers of materials that are suitable for use on difficult/hard tissues such as cartilage and bone. In other embodiments, the end-effector may include a surface treatment that has a roughness $R_A$ that is suitable for use on difficult/hard tissues such as cartilage and bone.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present disclosure.

Any of the end-effectors described herein (e.g., blades 112, 212, 312, 412, 512, 612, 712, 912, 1012) may be reconditioned for reuse after at least one use. In one embodiment, reconditioning can include obtaining an ultrasonic surgical blade and applying at least one layer of a first material on at least a portion of the body 108 to form a lubricious coating on the outer surface of the body 108. The lubricious coating may be applied in accordance with any suitable material application techniques, including material application techniques described herein. Then, sterilizing the ultrasonic surgical blade and storing the ultrasonic surgical blade in a sterile container. In another embodiment, reconditioning can include obtaining an ultrasonic surgical blade and forming at least one surface treatment on at least a portion of the body 108 to produce a frictional coating on the outer surface of the body 108. The surface treatment may be applied in accordance with any suitable surface treatment techniques, including the surface treatment techniques described herein. Then, sterilizing the ultrasonic surgical blade and storing the ultrasonic surgical blade in a sterile container.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam. Accordingly, in one embodiment, an ultrasonic surgical blade comprising a body having a proximal end, a distal end, and an outer surface, the distal end is movable relative to a longitudinal axis in accordance with ultrasonic vibrations applied to the proximal end, and a lubricious coating being formed on at least a portion of the outer surface of the body, is obtained. The ultrasonic surgical blade is then sterilized and stored in a sterile container. In another embodiment, an ultrasonic surgical blade comprising a body having a proximal end, a distal end, and an outer surface, the distal end is movable relative to a longitudinal axis by ultrasonic vibrations applied to the proximal end and a predetermined surface treatment having a predetermined surface roughness being formed on at least a portion of the body, is obtained. The ultrasonic surgical blade is then sterilized and stored in a sterile container.

Although various embodiments have been described herein, many modifications and variations to those embodiments may be implemented. For example, different types of end-effectors may be employed. In addition, combinations of the described embodiments may be used. For example, blade coatings may be formed of any combination of layer materials and surface treatments described herein. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method, comprising:
    obtaining an ultrasonic blade comprising a proximal end configured to receive ultrasonic vibrations, wherein the ultrasonic blade further comprises an outer surface comprising a tissue treatment region;
    applying a frictional surface treatment to at least a portion of the tissue treatment region; and applying a lubricious coating over at least a portion of the frictional surface treatment.

2. The method of claim 1, wherein applying the frictional surface treatment comprises roughening at least a portion of the tissue treatment region to enhance adhesion of the lubricious coating.

3. The method of claim 2, wherein the tissue treatment region defines a first coefficient of friction relative to a tissue before application of the frictional surface treatment, wherein the tissue treatment region defines a second coefficient of friction relative to the tissue after application of the frictional surface treatment and before application of the lubricious coating, and wherein the second coefficient of friction is greater than the first coefficient of friction.

4. The method of claim 3, wherein the tissue treatment region defines a third coefficient of friction relative to the tissue after application of the lubricious coating, and wherein the third coefficient of friction is less than the first coefficient of friction.

5. The method of claim 1, wherein applying the frictional surface treatment comprises roughening at least a portion of the tissue treatment region to a surface roughness of about 16 μin to about 256 μin.

6. The method of claim 1, wherein applying the frictional surface treatment comprises roughening at least a portion of the tissue treatment region to a surface roughness of less than 32 μin.

7. The method of claim 1, wherein the lubricious coating comprises a polymeric material.

8. The method of claim 1, wherein the ultrasonic blade further comprises a body extending along an axis, and wherein the axis defines at least one curve.

9. The method of claim 1, further comprising sterilizing the ultrasonic blade.

10. The method of claim 9, further comprising storing the sterilized ultrasonic blade in a sterile container.

11. A method comprising:
obtaining an ultrasonic blade comprising a proximal end configured to receive ultrasonic vibrations, wherein the ultrasonic blade further comprises an outer surface comprising a tissue treatment region;
applying a surface treatment to at least a portion of the tissue treatment region; and
applying a lubricious coating to at least a portion of the tissue treatment region, wherein the surface treatment is configured to improve adhesion of the lubricious coating to the outer surface.

12. The method of claim 11, wherein the surface treatment is selected from the following group: peening, sand blasting, micro blasting, bead blasting, knurling, engraving, chemical treatment such as acid or base etching, laser etching, plasma etching, corona discharge etching, heat etching, carving, scoring, vibratory deburring, abrasive flow machining, and combinations thereof.

13. The method of claim 11, wherein the tissue treatment region defines a first coefficient of friction relative to a tissue before application of the surface treatment, wherein the tissue treatment region defines a second coefficient of friction relative to the tissue after application of the surface treatment and before application of the lubricious coating, and wherein the second coefficient of friction is greater than the first coefficient of friction.

14. The method of claim 13, wherein the tissue treatment region defines a third coefficient of friction relative to the tissue after application of the lubricious coating, and wherein the third coefficient of friction is less than the first coefficient of friction.

15. The method of claim 11, wherein applying the surface treatment comprises roughening at least a portion of the tissue treatment region to a surface roughness of about 16 μin to about 256 μin.

16. The method of claim 11, wherein applying the surface treatment comprises roughening at least a portion of the tissue treatment region to a surface roughness of less than 32 μin.

17. The method of claim 1, wherein the lubricious coating comprises a thickness greater than 0.0001 inches and less than 0.010 inches.

18. The method of claim 11, wherein the lubricious coating comprises a thickness greater than 0.0001 inches and less than 0.010 inches.

* * * * *